(12) United States Patent
Mourad et al.

(10) Patent No.: US 6,875,176 B2
(45) Date of Patent: Apr. 5, 2005

(54) SYSTEMS AND METHODS FOR MAKING NONINVASIVE PHYSIOLOGICAL ASSESSMENTS

(75) Inventors: Pierre D. Mourad, Seattle, WA (US); Michel Kliot, Bellevue, WA (US); Ali Mesiwala, Seattle, WA (US); Rex Patterson, Kirkland, WA (US); Jeffrey G. Jarvik, Seattle, WA (US)

(73) Assignees: Aller Physionix Limited, Victoria (CA); University of Washington, Seattle, WA (US)

( * ) Notice: Subject to any disclaimer, the term of this patent is extended or adjusted under 35 U.S.C. 154(b) by 0 days.

(21) Appl. No.: 09/995,897

(22) Filed: Nov. 28, 2001

(65) Prior Publication Data

US 2002/0095087 A1 Jul. 18, 2002

Related U.S. Application Data

(60) Provisional application No. 60/253,959, filed on Nov. 28, 2000.

(51) Int. Cl.[7] .................................................. A61B 8/12
(52) U.S. Cl. ....................................................... 600/442
(58) Field of Search ................. 601/2, 3; 600/407–471; 367/7, 11, 130; 73/625, 626; 128/916

(56) References Cited

U.S. PATENT DOCUMENTS

| | | | |
|---|---|---|---|
| 3,872,858 A | 3/1975 | Hudson et al. ............. | 128/2 V |
| 4,043,321 A | 8/1977 | Soldner et al. ............. | 128/2 V |
| 4,771,792 A | 9/1988 | Seale ......................... | 128/774 |
| 4,984,567 A | 1/1991 | Kageyama et al. .... | 128/660.02 |

(Continued)

FOREIGN PATENT DOCUMENTS

| WO | 0057766 | 10/2000 |
|---|---|---|
| WO | 0068647 | 11/2000 |
| WO | WO 01/89358 A2 | 11/2001 |

OTHER PUBLICATIONS

Czosnyka, Marek Ph.D., et al., "Monitoring of Cerebral Autoregulation in Head–Injured Patients," *Stroke*, vol. 27, No. 10, pp. 1829–1834 (Oct. 1996).

Nichols, John S., et al., "Detection of Impaired Cerebral Autoregulation Using Spectral Analysis of Intracranial Pressure Waves," *Journal of Neurotrauma*, vol. 13, No. 8, pp. 439–456 (1996).

Daley, M.L., et al., "Correlation Coefficient Between Intracranial and Arterial Pressures: A Gauge of Cerebral Vascular Dilation," *Acta Neurochir*, [Suppl] vol. 71, pp. 285–288 (1998).

(Continued)

*Primary Examiner*—Ali Imam
(74) *Attorney, Agent, or Firm*—Ann W. Speckman; Speckman Law Group PLLC

(57) ABSTRACT

Systems and methods for assessment of tissue properties, noninvasively, by acquiring data relating to at least one aspect of intrinsic and/or induced tissue displacement, or associated biological responses, are provided. Data relating to tissue displacement and associated biological changes may be acquired by detecting acoustic properties of tissue using ultrasound interrogation pulses, preferably in a scatter or Doppler detection mode. Based on this data, tissue properties are assessed, characterized and monitored. Specific applications for systems and methods of the present invention include non-invasive assessment and monitoring of intracranial pressure (ICP), arterial blood pressure (ABP), CNS autoregulation status, vasospasm, stroke, local edema, infection and vasculitis, as well as diagnosis and monitoring of diseases and conditions that are characterized by physical changes in tissue properties. Methods and systems for localizing physiological condition(s) and/or biological response (s), such as pain, by targeting and selectively probing tissues using the application of focused ultrasound are also provided.

54 Claims, 7 Drawing Sheets

U.S. PATENT DOCUMENTS

| | | |
|---|---|---|
| 5,074,310 A | 12/1991 | Mick .......................... 128/748 |
| 5,086,775 A | 2/1992 | Parker et al. ............... 128/660 |
| 5,099,848 A | 3/1992 | Parker et al. .......... 128/661.07 |
| 5,117,835 A | 6/1992 | Mick .......................... 128/748 |
| 5,241,964 A | 9/1993 | McQuilkin ................. 128/672 |
| RE34,663 E | 7/1994 | Seale ......................... 128/774 |
| 5,388,583 A | 2/1995 | Raguauskas et al. ... 128/661.05 |
| 5,411,028 A | 5/1995 | Bonnefous ............ 128/661.08 |
| 5,524,636 A | 6/1996 | Sarvazyan et al. .......... 128/774 |
| 5,579,774 A | 12/1996 | Miller et al. ................ 128/667 |
| 5,606,971 A | 3/1997 | Sarvazyan .................. 128/660 |
| 5,617,873 A | 4/1997 | Yost et al. .................. 128/748 |
| 5,678,565 A | 10/1997 | Sarvazyan .................. 128/774 |
| 5,685,313 A | 11/1997 | Mayevsky .................. 128/665 |
| 5,749,364 A | 5/1998 | Sliwa, Jr. et al. ....... 128/662.02 |
| 5,806,521 A | 9/1998 | Morimoto et al. .......... 128/661 |
| 5,807,250 A | 9/1998 | Ohtomo et al. ............. 600/407 |
| 5,810,731 A | 9/1998 | Sarvazyan et al. .......... 600/438 |
| 5,830,131 A | 11/1998 | Caro et al. .................. 600/300 |
| 5,836,894 A | 11/1998 | Sarvazyan .................. 600/587 |
| 5,840,018 A | 11/1998 | Michaeli ..................... 600/300 |
| 5,873,840 A | 2/1999 | Neff ........................... 600/561 |
| 5,903,516 A | 5/1999 | Greenleaf et al. ............. 367/92 |
| 5,916,171 A | 6/1999 | Mayevsky .................. 600/476 |
| 5,919,144 A | 7/1999 | Bridger et al. .............. 600/561 |
| 5,921,928 A | 7/1999 | Greenleaf et al. .......... 600/437 |
| 5,951,476 A | 9/1999 | Beach ........................ 600/437 |
| 5,951,477 A | 9/1999 | Ragauskas et al. .......... 600/438 |
| 6,020,675 A | 2/2000 | Yamashita et al. .......... 310/358 |
| 6,039,691 A | 3/2000 | Walker et al. ............... 600/452 |
| 6,042,545 A | 3/2000 | Hossack et al. |
| 6,042,556 A | 3/2000 | Beach et al. ..................... 601/3 |
| 6,066,097 A | 5/2000 | Glenn et al. ................. 600/443 |
| 6,086,533 A | 7/2000 | Madson et al. ............. 600/438 |
| 6,110,114 A | 8/2000 | Nock et al. |
| 6,113,559 A * | 9/2000 | Klopotek ....................... 601/3 |
| 6,117,089 A | 9/2000 | Sinha |
| 6,129,682 A | 10/2000 | Borchert et al. ............ 600/561 |
| 6,328,694 B1 * | 12/2001 | Michaeli ..................... 600/438 |
| 6,352,507 B1 | 3/2002 | Torp et al. |
| 6,527,717 B1 | 3/2003 | Jackson et al. |
| 6,692,443 B2 | 2/2004 | Crutchfield et al. |
| 6,723,051 B2 | 4/2004 | Davidson et al. |
| 2004/0049105 A1 | 3/2004 | Crutchfield et al. |

OTHER PUBLICATIONS

Ferguson, John, "The Promise of Portable MRI," *California Institute of Technology—Engineering and Science*, vol. LXIV, No. 2, pp. 28–33 (Nov. 2, 2001).

Wayengerg, J.-L., "Non-Invasisve Measurement of Intercranial Pressure in eonates and Infants: Experience with the Rotterdam Teletransducer," *Acta Neurochir*, [Suppl] vol. 71, pp. 70–73 (1998).

Nightingale, Kathryn R., et al., "On the Feasibility of Remote Palpation Using Acoustic Radiation Force," *J. Acoust. Soc. Am.*, vol. 110, No. 1, pp. 625–634 (Jul. 2001).

Fry, F. J., et al., "Threshold Ultrasonic Dosages for Structural Changes in the Mammalian Brain," *J. Acoust. Soc. Am.*, vol. 48, No. 6, (Part 2), pp. 1413–1417 (May 1970).

Davies, Iolo ab Ithel, et al., "Applicaiton of Focused Ultrasound for Research on Pain," *Pain*, vol. 67, pp. 17–27 (1996).

Parker, Kevin J. Ph.D., "Sonoelasticity Imaging," http://www.ee.Rochester.edu:8080/projects/sonoelasticity/patents.html, (printed Oct. 17, 2000).

Sujimoto, Tsuneyhoshi et al., "Tissue Hardness Measurement Using the Radiation Force of Focused Ultrasound," *Tokyo Institute of Technology, Research Laboratory of Precision Machinery and Electronics Ultrasonics Symposium*, pp. 1377–1380 (1990).

Braukus, Michael et al., "NASA Tests Painless Ways of Measuring Intracranial Pressure," http://www.qadas.com/qadas/nasa/nasa–hm/0092.html (printed Oct. 3, 2000).

Fatemi, Mostafa et al., "Ultrasound–Stimulated Vibro–Acoustic Spectrography," *Science*, vol. 280, No. 3, pp. 82–85 (Apr. 1998).

Schmidt, Bernhard et al., "Noninvasive Prediction of Intracranial Pressure Curves Using Transcranial Doppler Ultrasonography and Blood Pressure Curves," *Stroke*, vol. 28, No. 12, pp. 2465–2472 (Dec. 1997).

IBM Technical Disclosure Bulletin, "Noninvasisve Pressure Measurement," http://www.delphion.com/tdbs/tdb?&order+78A=00387 (printed Nov. 22, 2000).

M. Czosnyka, P., et al., "Continuous Monitoring of Cerebrovascular Pressure–Reactivity in Head Injury," *Acta Neurochir*, [Suppl] vol. 71, pp. 74–77 (1998).

* cited by examiner

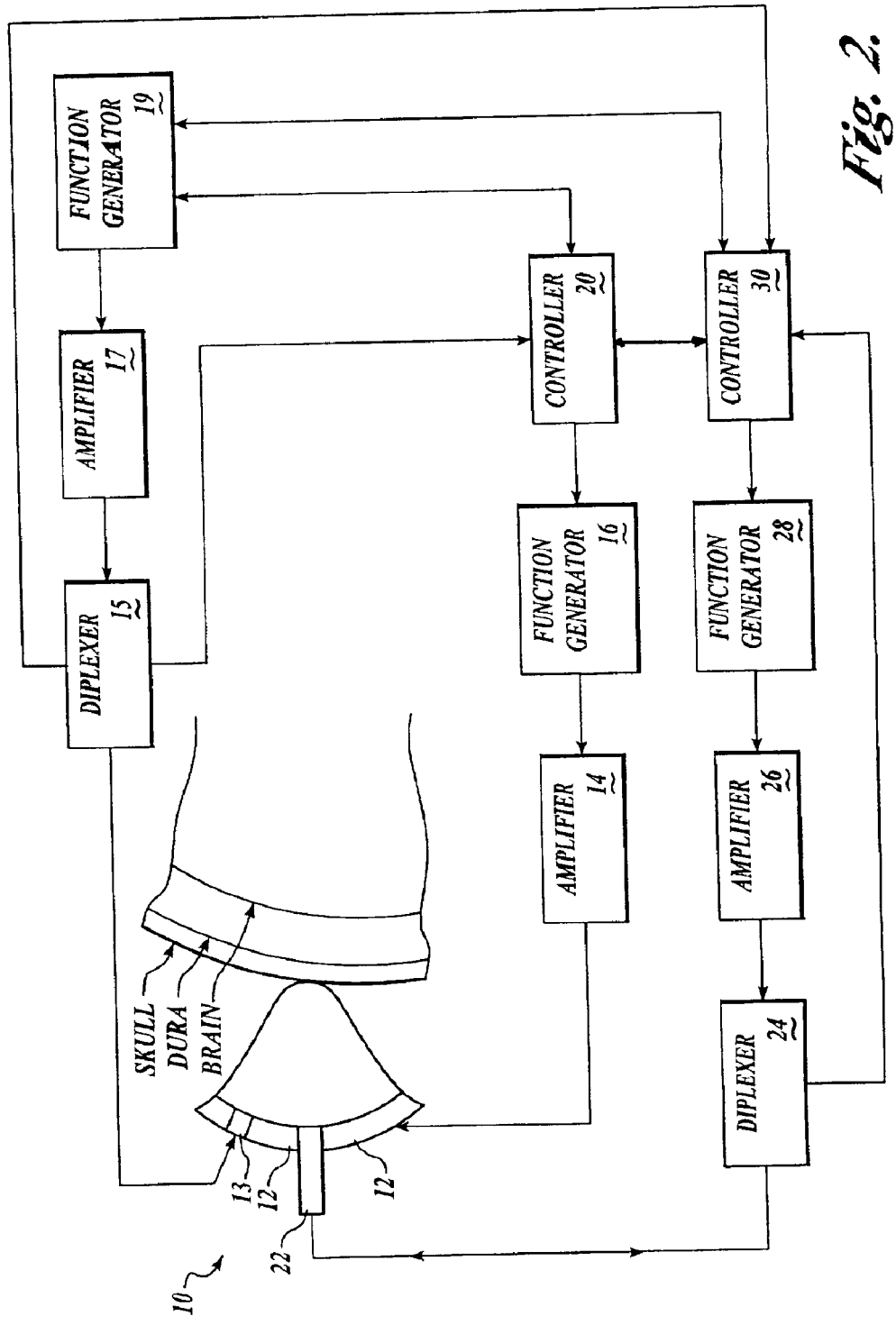

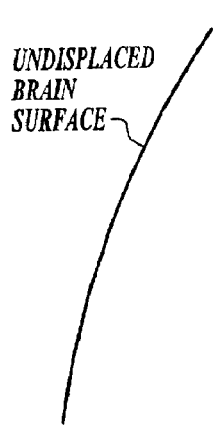 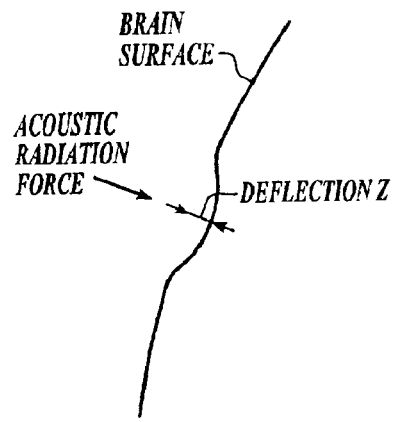 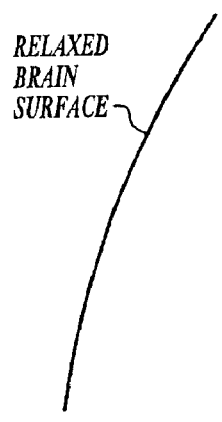
*Fig. 5A.*    *Fig. 5B.*    *Fig. 5C.*
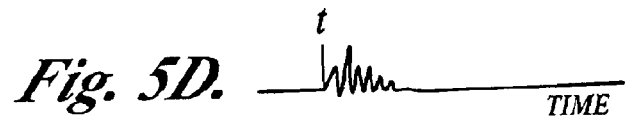
*Fig. 5D.*
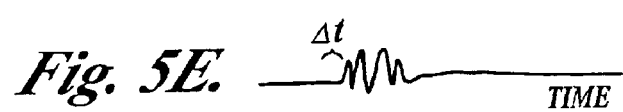
*Fig. 5E.*
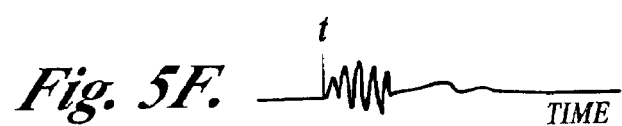
*Fig. 5F.*

SYSTEMS AND METHODS FOR MAKING NONINVASIVE PHYSIOLOGICAL ASSESSMENTS

CROSS-REFERENCE TO RELATED APPLICATION

This application claims priority under 35 U.S.C. 119(e) to U.S. patent application Ser. No. 60/253,959, filed Nov. 28, 2000.

GOVERNMENT SUPPORT

This invention was made with government support under ONR Contract Number N00014-96-1-0630 awarded by the Office of Naval Research. The government has certain rights in the invention.

Subject matter diclosed in this application was supported by federally sponsored research and development funding. The U.S. Government may have certain rights in the invention as provided for by the terms of U.S. Navy Contract N00014-96-1-0630 issued by the Office of Naval Research.

TECHNICAL FIELD OF THE INVENTION

An objective of this invention is to assess medically relevant physiological properties of target tissues by detecting exogenous (induced) and/or endogenous (intrinsic) displacement and/or compression of tissue. Another objective is to spatially localize tissues having certain physiological properties or producing certain biological responses to the application of focused ultrasound (acoustic probing or palpation). The present invention thus relates to systems and methods for noninvasive localization, assessment and monitoring of tissue properties and physiological conditions by detecting at least one parameter relating to intrinsic and/or induced tissue displacement and/or associated biological responses.

In one embodiment, acoustic properties of tissues are related to intrinsic and/or induced tissue displacement or associated biological responses, and are thereby related to tissue properties and physiological conditions. These systems and methods are especially effective for assessing central nervous system (CNS) tissue. Specific applications for systems and methods of the present invention include non-invasive assessment and monitoring of acute, chronic and traumatic damage or injury to the CNS, intracranial pressure (ICP), arterial blood pressure (ABP), CNS autoregulation status or capacity, cerebral perfusion pressure (CPP), vasospasm, stroke, local edema, infection and vasculitus, as well as diagnosis and monitoring of diseases and conditions that are characterized by physical changes in tissue properties, such as Alzheimer's disease, multiple sclerosis, ischemic conditions, hyopoxic conditions, subdural and epidural and subarachnoid hemotomas, intracerebral hemorrhage, tumors and other intra-cranial masses, and the like. Detection of intrinsic and/or induced displacements of other tissue types, including peripheral nerve tissue, heart tissue, and other non-bony tissues, may also be used to assess and monitor non-CNS physiological conditions.

In another embodiment, methods and systems for localizing physiological condition(s) and/or biological response (s) are provided. Internal tissues are targeted and selectively stimulated, by application of focused ultrasound, to elicit pain responses. Because an acoustic beam may be targeted and focused, the source of pain may be localized and identified by acoustically probing individual sites within generalized sites of pain. Targeted acoustic probing of focused sites may be assisted, or visualized, using imaging techniques such as ultrasound imaging or magnetic resonance imaging (MRI). These techniques for pain localization are particularly effective for localizing and identifying the source(s) of pain in the spine and in other joints, and at various structurally complex sites, and for localizing and identifying the source of internal pain produced, for example, by appendicitis, cholecystitis, pelvic inflammatory disease, lymphadenopathies, peripheral nerve-related conditions, and the like.

BACKGROUND OF THE INVENTION

Methods and systems for determining and characterizing various systems and tissue properties are known. Characterization of internal tissues using non-invasive and non-traumatic techniques is challenging in many areas. Non-invasive detection of various cancers remains problematic and unreliable. Similarly, non-invasive assessment and monitoring of intracranial pressure is also a practical challenge, despite the efforts devoted to developing such techniques.

Ultrasound imaging is a non-invasive, diagnostic modality that is capable of providing information concerning tissue properties. In the field of medical imaging, ultrasound may be used in various modes to produce images of objects or structures within a patient. In a transmission mode, an ultrasound transmitter is placed on one side of an object and the sound is transmitted through the object to an ultrasound receiver. An image may be produced in which the brightness of each image pixel is a function of the amplitude of the ultrasound that reaches the receiver (attenuation mode), or the brightness of each pixel may be a function of the time required for the sound to reach the receiver (time-of-flight mode). Alternatively, if the receiver is positioned on the same side of the object as the transmitter, an image may be produced in which the pixel brightness is a function of the amplitude of reflected ultrasound (reflection or backscatter or echo mode). In a Doppler mode of operation, the tissue (or object) is imaged by measuring the phase shift of the ultrasound reflected from the tissue (or object) back to the receiver.

Ultrasonic transducers for medical applications are constructed from one or more piezoelectric elements activated by electrodes. Such piezoelectric elements may be constructed, for example, from lead zirconate titanate (PZT), polyvinylidene diflouride (PVDF), PZT ceramic/polymer composite, and the like. The electrodes are connected to a voltage source, a voltage waveform is applied, and the piezoelectric elements change in size at a frequency corresponding to that of the applied voltage. When a voltage waveform is applied, the piezoelectric elements emit an ultrasonic wave into the media to which it is coupled at the frequencies contained in the excitation waveform. Conversely, when an ultrasonic wave strikes the piezoelectric element, the element produces a corresponding voltage across its electrodes. Numerous ultrasonic transducer constructions are known in the art.

When used for imaging, ultrasonic transducers are provided with several piezoelectric elements arranged in an array and driven by different voltages. By controlling the phase and amplitude of the applied voltages, ultrasonic waves combine to produce a net ultrasonic wave that travels along a desired beam direction and is focused at a selected point along the beam. By controlling the phase and the amplitude of the applied voltages, the focal point of the beam can be moved in a plane to scan the subject. Many such ultrasonic imaging systems are well known in the art.

An acoustic radiation force is exerted by an acoustic wave on an object in its path. The use of acoustic radiation forces produced by an ultrasound transducer has been proposed in connection with tissue hardness measurements. See Sugimoto et al., "Tissue Hardness Measure Using the Radiation Force of Focused Ultrasound", *IEEE Ultrasonics Symposium*, pp. 1377–80, 1990. This publication describes an experiment in which a pulse of focused ultrasonic radiation is applied to deform the object at the focal point of the transducer. The deformation is measured using a separate pulse-echo ultrasonic system. Measurements of tissue hardness are made based on the amount or rate of object deformation as the acoustic force is continuously applied, or by the rate of relaxation of the deformation after the force is removed.

Another system is disclosed by T. Sato, et al., "Imaging of Acoustical Nonlinear Parameters and Its Medical and Industrial Applications: A Viewpoint as Generalized Percussion," Acoustical Imaging, Vo. 20, pg. 9–18, Plenum Press, 1993. In this system, a lower frequency wave (350 kHz) is used as a percussion force, and an ultrasonic wave (5 MHz) is used in a pulse-echo mode to produce an image of the subject. The percussion force perturbs second order nonlinear interactions in tissues, which may reveal more structural information than conventional ultrasound pulse-echo systems.

Fatemi and Greenleaf reported an imaging technique that uses acoustic emission to map the mechanical response of an object to local cyclic radiation forces produced by interfering ultrasound beams. The object is probed by arranging the intersection of two focused, continuous-wave ultrasound beams of different frequencies at a selected point on the object. Interference in the intersection region of the two beams produces modulation of the ultrasound energy density, which creates a vibration in the object at the selected region. The vibration produces an acoustic field that can be measured. The authors speculate that ultrasound-stimulated vibro-acoustic spectrography has potential applications in the non-destructive evaluation of materials, and for medical imaging and noninvasive detection of hard tissue inclusions, such as the imaging of arteries with calcification, detection of breast microcalcifications, visualization of hard tumors, and detection of foreign objects.

U.S. Pat. Nos. 5,903,516 and 5,921,928 (Greenleaf et al.) disclose a method and system for producing an acoustic radiation force at a target location by directing multiple high frequency sound beams to intersect at the desired location. A variable amplitude radiation force may be produced using variable, high frequency sound beams, or by amplitude modulating a high frequency sound beam at a lower, baseband frequency. The mechanical properties of an object, or the presence of an object, may be detected by analyzing the acoustic wave that is generated from the object by the applied acoustic radiation force. An image of the object may be produced by scanning the object with high frequency sound beams and analyzing the acoustic waves generated at each scanned location. The mechanical characteristics of an object may also be assessed by detecting the motion produced at the intersections of high frequency sound beams and analyzing the motion using Doppler ultrasound and nuclear magnetic resonance imaging techniques. Variations in the characteristics of fluids (e.g. blood), such as fluid temperature, density and chemical composition can also be detected by assessing changes in the amplitude of the beat frequency signal. Various applications are cited, including detection of atherosclerosis, detection of gas bubbles in fluids, measurement of contrast agent concentration in the blood stream, object position measurement, object motion and velocity measurement, and the like. An imaging system is also disclosed.

U.S. Pat. No. 6,039,691 (Walker et al.) discloses methods and apparatus for soft tissue examination employing an ultrasonic transducer for generating an ultrasound pulse that induces physical displacement of viscous or gelatinous biological fluids and analysis techniques that determine the magnitude of the displacement. The transducer receives ultrasonic echo pulses and generates data signals indicative of the tissue displacement. This apparatus and method is particularly useful for examining the properties of a subject's vitreous body, in connection with the evaluation and/or diagnosis of ocular disorders, such as vitreous traction.

U.S. Pat. No. 5,086,775 (Parker et al.) describes a system in which a low frequency vibration source is used to generate oscillations in an object, and a coherent or pulsed ultrasound imaging system is used to detect the spatial distribution of the vibration amplitude or speed of the object in real-time. In particular, the reflected Doppler shifted waveform generated is used to compute the vibration amplitude and frequency of the object on a frequency domain estimator basis, or on a time domain estimator basis. Applications of this system include examination of passive structures such as aircraft, ships, bridge trusses, as well as soft tissue imaging, such as breast imaging.

Several U.S. Patents to Sarvazyan relate to methods and devices for ultrasonic elasticity imaging for noninvasively identifying tissue elasticity. Tissue having different elasticity properties may be identified, for example, by simultaneously measuring strain and stress patterns in the tissue using an ultrasonic imaging system in combination with a pressure sensing array. The ultrasonic scanner probe with an attached pressure sensing array may exert pressure to deform the tissue and create stress and strain in the tissue. This system may be used, for example, to measure mechanical parameters of the prostate. U.S. Patents to Sarvazyan also describe shear wave elasticity imaging using a focused ultrasound transducer that remotely induces a propagating shear wave in tissue. Shear modulus and dynamic shear viscosity at a given site may be determined from the measured values of velocity and attenuation of propagating shear waves at that site.

Intracranial Pressure

Normal, healthy mammals, particularly humans, have a generally constant intracranial volume and, hence, a generally constant intracranial pressure. Various conditions produce changes in the intracranial volume and, consequently, produce changes in intracranial pressure. Increases in intracranial pressure may produce conditions under which the intracranial pressure rises above normal and approaches or even equals the mean arterial pressure, resulting in reduced blood flow to the brain. Elevated intracranial pressure not only reduces blood flow to the brain, but it also affects the normal metabolism of cells within the brain. Under some conditions, elevated intracranial pressures may cause the brain to be mechanically compressed, and to herniate.

The most common cause of elevated intracranial pressure is head trauma. Additional causes of elevated intracranial pressure include shaken-baby syndrome, epidural hematoma, subdural hematoma, brain hemorrhage, meningitis, encephalitis, lead poisoning, Reye's syndrome, hypervitaminosis A, diabetic ketoacidosis, water intoxication, brain tumors, other masses or blood clots in the cranial cavity, brain abcesses, stroke, ADEM (acute disseminated encephalomyelitis), metabolic disorders, hydrocephalus, and dural sinus and venous thrombosis. Changes in intracranial pressure, particularly elevated intracranial pressure, are very serious and may be life threatening. They require immediate treatment and continued monitoring.

Conventional intracranial pressure monitoring devices include: epidural catheters; subarachnoid bolt/screws; ventriculostomy catheters; and fiberoptic catheters. All of these methods and systems are invasive. An epidural catheter may be inserted, for example, during cranial surgery. The epidural catheter has a relative low risk of infection and it does not require transducer adjustment with head movement, but the accuracy of sensing decreases through dura, and it is unable to drain CSF. The subarachnoid bolt/screw technique requires minimal penetration of the brain, it has a relatively low risk of infection, and it provides a direct pressure measurement, but it does require penetration of an intact skull and it poorly drains CSF. The ventriculostomy catheter technique provides CSF drainage and sampling and it provides a direct measurement of intracranial pressure, but the risks of infection, intracerebral bleeding and edema along the cannula track are significant, and it requires transducer repositioning with head movement. Finally, the fiber optic catheter technique is versatile because the catheter may be placed in the ventricle or in the subarachnoid space, and it does not require adjustment of the transducer with head movement, but it requires a separate monitoring system, and the catheter is relatively fragile. All of these conventional techniques require invasive procedures and none is well suited to long term monitoring of intracranial pressure on a regular basis. Moreover, these procedures can only be performed in hospitals staffed by qualified neurosurgeons. In addition, all of these conventional techniques measure ICP locally, and presumptions are made that the local ICP reflects the whole brain ICP.

Various methods and systems have been developed for measuring intracranial pressure indirectly and/or non-invasively. Several of these methods involve ultrasound techniques. U.S. Pat. No. 5,951,477 of Ragauskas et al., for example, discloses an apparatus for non-invasively measuring intracranial pressure using an ultrasonic Doppler device that detects the velocities of the blood flow inside the optic artery for both intracranial and extracranial optic artery portions. The eye in which the blood flow is monitored is subjected to a small pressure, which is sufficient to equalize the blood flow measurements of the intracranial and extracranial portions of the optic artery. The pressure at which such equalization occurs is disclosed to be an acceptable indication of the intracranial pressure. In practice, a pressurized chamber is sealed to the perimeter around an eye and the pressure in the chamber is controlled to equalize blood velocities of intracranial and extracranial portions of the optic artery.

U.S. Pat. No. 5,388,583, to Ragauskas et al., discloses an ultrasonic non-invasive technique for deriving the time dependencies of characteristics of certain regions in the intracranial medium. Precise measurements of the transit travel times of acoustic pulses are made and processed to extract variable portions indicative of, for example, the pulsatility due to cardiac pulses of a basal artery or a cerebroventricle or the variation in the pressure of brain tissue, as well as changes in the cross-sectional dimension of the basal artery and ventricle. Frequency and phase detection techniques are also described.

U.S. Pat. No. 5,411,028 to Bonnefous discloses an ultrasonic echograph used for the measurement of various blood flow and blood vessel parameters that provide information for calculating determinations relating to the elasticity or compliance of an artery and its internal pressure.

U.S. Pat. No. 5,117,835 to Mick discloses a method and apparatus for non-invasively measuring changes in intracranial pressure by measuring changes in the natural frequency and frequency response spectrum of the skull bone. Changes in the natural frequency and frequency response spectrum of the skull are measured by applying a mechanical forced oscillation stimulus that creates a mechanical wave transmission through the bone, and then sensing the frequency response spectrum. Comparison of spectral response data over time shows trends and changes in ICP.

U.S. Pat. No. 6,129,682 to Borchert et al. discloses a method for non-invasively determining ICP based on intraocular pressure (IOP) and a parameter of the optic nerve, such as thickness of the retinal nerve fiber layer or anterior-posterior position of the optic nerve head.

U.S. Pat. No. 6,086,533 to Madsen et al. discloses systems for non-invasive measurement of blood velocity based on the Doppler shift, and correlation of blood velocity before and after the manual application of an externally applied pressure, to provide a measure of intracranial pressure, ophthalmic pressure, and various other body conditions affecting blood perfusion.

U.S. Pat. No. 5,919,144 to Bridger et al. discloses a non-invasive apparatus and method for measuring intracranial pressure based on the properties of acoustic signals that interacted with the brain, such as acoustic transmission impedance, resonant frequency, resonance characteristics, velocity of sound, and the like. Low intensity acoustic signals having frequencies of less than 100 kHz are used.

U.S. Pat. No. 4,984,567 to Kageyama et al. discloses an apparatus for measuring intracranial pressure using ultrasonic waves. Data from interference reflection waves caused by multiple reflections of incident ultrasonic waves at the interstitial boundaries within the cranium are analyzed for frequency, and the time difference between the element waves of the interference reflection wave is calculated and provided as output. The device described incorporates an electrocardiograph for detecting the heart beat, a pulser for generating a voltage pulse, an ultrasonic probe for receiving the pulse and transmitting an ultrasonic pulse into the cranium and receiving the echo of the incident wave, and a processor for making various calculations.

U.S. Pat. No. 5,951,476 to Beach provides a method for detecting brain microhemorrhage by projecting bursts of ultrasound into one or both of the temples of the cranium, or into the medulla oblongata, with the readout of echoes received from different depths of tissue displayed on a screen. The readouts of the echoes indicated accrued microshifts of the brain tissue relative to the cranium. The timing of the ultrasound bursts is required to be synchronized with the heart pulse of the patient.

U.S. Pat. No. 6,042,556 discloses a method for determining phase advancement of transducer elements in high intensity focused ultrasound. Specific harmonic echoes are distributed in all directions from the treatment volume, and the temporal delay in the specific harmonic echoes provides a measure of the propagation path transit time to transmit a pulse that converges on the treatment volume.

U.S. Pat. No. 3,872,858 discloses an echoencephalograph for use in the initial diagnosis of midline structure lateral shift that applies an ultrasonic pulse to a patient's head, the pulse traveling to a predetermined structure and being partially reflected as an echo pulse. Shifts are determined by measuring the travel time of the echo pulse.

U.S. Pat. No. 4,984,567 describes an apparatus for measuring intracranial pressure based on the ultrasonic assay of changes in the thickness of the dura covering the brain induced by changes in ICP.

Michaeli et al., in PCT International Publication No. WO 00/68647, describe determination of ICP, noninvasively, using ultrasonic backscatter representative of the pulsation of a ventricle in the head of the patient. This includes the analysis of echo pulsograms (EPG).

NASA has also worked on the development of methods and systems for noninvasive intracranial pressure measurement. Intracranial pressure dynamics are important for understanding adjustments to altered gravity. ICP may be elevated during exposure to microgravity conditions. Symptoms of space adaptation syndrome are similar to those of elevated intracranial pressure, including headache, nausea and projectile vomiting. The hypothesis that ICP is altered in microgravity environments is difficult to test, however, as a result of the invasive nature of conventional ICP measurement techniques. NASA has therefore developed a modified pulsed phase-locked loop (PPLL) method for measuring ICP based on detection of skull movements which occur with fluctuations in ICP. Detection of skull pulsation uses an ultrasound technique in which slight changes in the distance between an ultrasound transducer and a reflecting target are measured. The instrument transmits a 500 kHz ultrasonic tone burst through the cranium, which passes through the cranial cavity, reflects off the inner surface of the opposite side of the skull, and is received by the same transducer. The instrument compares the phase of emitted and received waves and alters the frequency of the next stimulus to maintain a 90 degree phase difference between the ultrasound output and the received signal. Experimental data demonstrated that the PPLL output was highly and predictably related to directly measured ICP.

Arterial Blood Pressure

Arterial blood pressure (ABP) is a fundamental objective measure of the state of an individual's health. Indeed, it is considered a "vital sign" and is of critical importance in all areas of medicine and healthcare. The accurate measure of ABP assists in determination of the state of cardiovascular and hemodynamic health in stable, urgent, emergent, and operative conditions, indicating appropriate interventions to maximize the health of the patient.

Currently, ABP is most commonly measured noninvasively using a pneumatic cuff, often described as pneumatic plethysmography or Kortkoff's method. While this mode of measurement is simple and inexpensive to perform, it does not provide the most accurate measure of ABP, and it is susceptible to artifacts resulting from the condition of arterial wall, the size of the patient, the hemodynamic status of the patient, and autonomic tone of the vascular smooth muscle. Additionally, repeated cuff measurements of ABP result in falsely elevated readings of ABP, due to vasoconstriction of the arterial wall. To overcome these problems, and to provide a continuous measure of ABP, invasive arterial catheters are used. While such catheters are very reliable and provide the most accurate measure of ABP, they require placement by trained medical personnel, usually physicians, and they require bulky, sophisticated, fragile, sterile instrumentation. Additionally, there is a risk of permanent arterial injury causing ischemic events when these catheters are placed. As a result, these invasive monitors are only used in hospital settings and for patients who are critically ill or are undergoing operative procedures.

U.S. Pat. No. 4,869,261 to Penaz discloses a method for automatic, non-invasive determination of continuous arterial blood pressure in arteries compressible from the surface by first determining a set point with a pressure cuff equipped with a plethysmographic gauge of vascular volume and then maintaining the volume of the measured artery constant to infer arterial blood pressure. A generator producing pressure vibrations superimposed on the basic blood pressure wave, and the changes in the oscillations of the blood pressure wave are monitored by an active servo-system that constantly adjusts the cuff pressure to maintain constant arterial volume; thus, the frequency of vibration of the blood pressure wave that is higher than the highest harmonic component of the blood pressure wave is used to determine arterial blood pressure.

U.S. Pat. No. 4,510,940 to Wesseling discloses a method for correcting the cuff pressure in the indirect, non-invasive and continuous measurement of the blood pressure in a part of the body by first determining a set-point using a plethysmograph in a fluid-filled pressure cuff wrapped around an extremity and then adjusting a servo-reference level as a function of the shape of the plethysmographic signal, influenced by the magnitude of the deviation of the cuff pressure adjusted in both open and closed systems.

U.S. Pat. No. 5,241,964 to McQuilkin discloses a method for a non-invasive, non-occlusive method and apparatus for continuous determination of arterial blood pressure using one or more Doppler sensors positioned over a major artery to determine the time-varying arterial resonant frequency and hence blood pressure. Alternative methods including the concurrent use of proximal and distal sensors, impedance plethysmography techniques, infrared percussion sensors, continuous oscillations in a partially or fully inflated cuff, pressure transducers or strain gauge devices applied to the arterial wall, ultrasonic imaging techniques which provide the time-varying arterial diameter or other arterial geometry which changes proportionately with intramural pressure, radio frequency sensors, or magnetic field sensors are also described.

U.S. Pat. No. 5,830,131 to Caro et al. discloses a method for determining physical conditions of the human arterial system by inducing a well-defined perturbation (exciter waveform) of the blood vessel in question and measuring a hemo-parameter containing a component of the exciter waveform at a separate site. The exciter consists of an inflatable bag that can exert pressure on the blood vessel of interest, and is controlled by a processor. Physical properties such as cardiovascular disease, arterial elasticity, arterial thickness, arterial wall compliance, and physiological parameters such as blood pressure, vascular wall compliance, ventricular contractions, vascular resistance, fluid volume, cardiac output, myocardial contractility, etc. are described.

U.S. Pat. No. 4,646,754 to Seale discloses a method for non-invasively inducing vibrations in a selected element of the human body, including blood vessels, pulmonary vessels, and eye globe, and detecting the nature of the responses for determining mechanical characteristics of the element. Methods for inducing vibrations include mechanical drivers, while methods for measuring responses include ultrasound, optical means, and visual changes. Mechanical characteristics include arterial blood pressure, organ impedance, intra-ocular pressure, and pulmonary blood pressure.

U.S. Pat. No. 5,485,848 to Jackson et al. discloses a method and apparatus for non-invasive, continuous arterial blood pressure determination using a separable, diagnostically accurate blood pressure measuring device, such as a conventional pressure cuff, to initially calibrate the system and then measuring arterial wall movement caused by blood flow through the artery to determine arterial blood pressure. Piezoelectric devices are used in wristband device to convert wall motion signals to an electric form that can be analyzed to yield blood pressure.

U.S. Pat. No. 5,749,364 to Sliwa, Jr. et al. discloses a method and apparatus for the determination of pressure and tissue properties by utilizing changes in acoustic behavior of micro-bubbles in a body fluid, such as blood, to present pressure information. This invention is directed at the method of mapping and presenting body fluid pressure information in at least two dimensions and to an enhanced method of detecting tumors.

PCT International Patent Publication WO 00/72750 to Yang et al. discloses a method and apparatus for the non-invasive, continuous monitoring of arterial blood pressure using a finger plethysmograph and an electrical impedance photoplethysmograph to monitor dynamic behavior of arterial blood flow. Measured signals from these sensors on an arterial segment are integrated to estimate the blood pressure in this segment based on a hemodynamic model that takes into account simplified upstream and downstream arterial flows within this vessel.

A noninvasive, continuous ABP monitor would provide medical personnel with valuable information on the hemodynamic and cardiovascular status of the patient in any setting, including the battlefield, emergency transport, clinic office, and triage clinics. Additionally, it would provide clinicians the ability to continuously monitor the ABP of a patient in situations where the risks of an invasive catheter are unwarranted or unacceptable (e.g., outpatient procedures, ambulance transports, etc.). Thus, the present invention is directed to methods and systems for the continuous assessment of ABP using non-invasive ultrasound techniques.

Autoregulation and Other Cerebral Conditions

ICP, blood pressure and autoregulation are intimately related. Well described cyclic phenomena known as "A", "B" and "C" waves, as well as "plateau" waves, which have been observed in transcranial Doppler (TCD) signals, relate ABP and ICP, for example.

The central nervous system (CNS) comprises various types of tissues and fluids. Blood flow to and from CNS tissues, such as the brain, is generally pulsatile, and the net volume of blood within the brain at any time point within the cardiac cycle is a function of systemic blood pressure and protective autoregulatory mechanisms of the brain vasculature. These various physical scales of cerebral vasculature, from the major arteries having diameters on the order of millimeters, to the arterioles having diameters on the order of microns, respond with different time scales and different levels of contribution to the determination of ICP and autoregulation. The different classes of cerebral vasculature also have different material properties, such as Young's moduli, which contribute to the different displacement properties in the brain. As brain tissue expands with the cardiac cycle, brain vasculature regulates the amount of blood that enters the brain and CSF simultaneously exits the cranial space and enters the spinal cord region, thereby maintaining a relatively constant ICP. As blood exits the brain, CSF flows back from the spinal cord space into the cranial region.

During this cyclical contraction and expansion of the brain, adequate blood flow to the brain must be maintained; thus, the cerebral vasculature dynamically adjusts its resistance to compensate for any changes in mean arterial blood pressure (MAP). The brain receives a substantially constant rate of blood flow, which is determined by cerebral perfusion pressure (CPP), where CPP=MAP−ICP over a wide range of mean arterial pressures. In this way, under normal conditions, the brain and its vasculature are capable of altering CPP in order to maintain proper blood flow to the brain. This is referred to as a normal state of autoregulation. When the ability to alter CPP to maintain proper blood flow to the brain is lost, autoregulation is abnormal and ICP becomes directly proportional to the mean arterial blood pressure.

Clinical determinations of whether autoregulation is "intact" or "impaired" are generally made by monitoring cerebral blood flow (CBF) and mean arterial blood pressure. CBF may be monitored using a transcranial Doppler (TCD) to measure blood flow velocities in large vessels in the brain, while MAP may be measured using any of the standard techniques. Physiological challenges may be administered to a patient to modulate—elevate or reduce—the systemic blood pressure, while the cerebral blood flow is monitored. Systemic blood pressure may be modulated, for example, by increasing pressure on an individual's extremities (e.g. applying a pressure cuff to an extremity), by administering a diuretic or another medication that alters systemic blood pressure, or the like. Systemic blood pressure may also be modulated by having an individual sneeze or cough. When autoregulation is "intact," the CBF remains generally constant over a wide range of mean arterial pressures; when autoregulation is "impaired," the CBF increases or decreases measurably over a range of mean arterial pressures. Conventional clinical autoregulation determination techniques are inexact and burdensome. Furthermore, measurement of CBF using transcranial Doppler techniques requires a skilled sonographer to find and maintain the focus of the equipment on large cerebral blood vessels while the patient, and the patient's CNS, may not be stationary.

Similarly, clinical determinations of conditions such as vasospasm, which may be indicative of stroke, local edema, infection and/or vasculitus, are generally made using transcranial Doppler (TCD) techniques. Vasospasm is a condition in which the cerebral vasculature contracts to such an abnormal degree that blood flow through the affected vessel is significantly reduced, although measured blood flow velocity may actually increase, causing transient and often permanent neurologic deficits (e.g., strokes). Vasospasm often results from subarachnoid hemorrhage stemming from the rupture of a cerebral aneurysm. Traditional TCD sonography uses the flow velocities in large cerebral vessels to assess the degree of vasospasm, as the smaller vessels are unable to be accurately localized and insonated with TCD. If the velocity of blood flow within the blood vessel of interest exceeds a certain value, vasospasm is inferred. In practice, TCD techniques are generally limited to assessing vasospasm in the large blood vessels at the base of the skull, since TCD techniques are not sufficiently sensitive to assess vasospasm in smaller blood vessels throughout the brain. The general clinical practice for confirming the presence of vasospasm, at present, is to perform a conventional cerebral angiogram. This is an extensive and expensive procedure. The present invention is thus additionally directed to systems and methods for assessing and monitoring the state of autoregulation in the setting of vasospasm and other conditions, such as stroke, local edema, infection and vasculitus, in CNS tissue.

Localization and Diagnosis of Sources of Pain

Pain is a frequent presenting symptom of numerous medical conditions, and although it plays an important role, often being the first alert that something is wrong, it can also be extremely nonspecific. There are multiple common conditions that would benefit from techniques for increasing the specificity and localization of pain. Low back pain (LBP) is a prime example of one common condition. The lifetime incidence of LBP is reported to be 60–90%, with an annual incidence of 5%. Each year, 14% of new patient visits to primary care physicians are for LBP, and nearly 13 million physician visits are related to complaints of chronic LBP, according to the National Center for Health Statistics. Unfortunately, it is difficult to identify the exact source of pain: several constituent pieces of a complex structure may be intimately adjoining, yet only one may be the source. While half of the American work force reports back pain, only about 20% of those cases result in a specific diagnosis of the source of pain. X-rays, computed tomography (CT) and magnetic resonance imaging (MRI) are the major diagnostic imaging tests for patients with low back pain and, while they can exquisitely depict anatomic abnormalities, the correlations between anatomic findings and patient symptoms are moderate at best.

In recent years, back pain specialists have begun to rely on invasive provocative tests in attempts to identify the "pain generator." Physicians insert needles into discs for discography to provoke pain and into facet and sacroiliac joints to provoke and then relieve pain through the injection of local anesthetics and steroids. These tests are frequently uncomfortable for the patient and carry the risk of infection and contrast reaction.

In the elderly, osteoporotic compression fractures are highly prevalent. The incidence is 700,000 fractures per year, generating 160,000 physician visits annually and over 5 million restricted activity days. Until recently, there were no good options for treatment. Vertebroplasty, which is the percutaneous injection of methylmethacrylate into the vertebral body is a new, promising treatment for these fractures. But in patients with multiple fractures, identifying the painful one may be difficult. Palpation on physical examination, bone scans and MRI have all been used, with varying degrees of success, in attempts to localize the painful fracture(s).

While back pain is a common painful condition that would benefit from increased specificity, other conditions exist as well. The diagnosis of appendicitis is difficult and imprecise. Despite the use of high-tech diagnostic imaging such as CT and ultrasound, a recent review in JAMA demonstrated no change in the false positive rate at appendectomy. Moreover, manual probing or palpation of the abdomen, with its poor specificity, is still a standard test, with mixed results.

Symptoms are what a patient reports spontaneously, whereas signs are elicited by an examining physician. In the conditions described above, pain symptoms signal a problem but frequently do not pinpoint the location of that problem. Therefore, in the case of back pain and other diseases, especially diseases having an inflammatory component (e.g. appendicitis, cholecystitis, pancreatitis, pelvic inflammatory disease, etc.), there is a need to precisely, reliably and in a non-invasive manner, stimulate individual constituent pieces of a complex structure within the body (e.g. discs, vertebral body, lamina and facets of the spine) to identify and spatially locate the exact source of the pain. Methods and systems of the present invention are thus additionally directed to localizing physiological conditions and/or biological responses, such as pain.

SUMMARY OF THE INVENTION

The present invention provides methods and systems for detecting induced and/or intrinsic tissue displacements and assessing physiological tissue properties based on data relating to induced and/or intrinsic tissue displacements and/or biological responses. Physiological properties of internal tissues may be assessed noninvasively using techniques of the present invention. Any tissue that experiences intrinsic tissue displacements resulting, for example, from the cardiac and/or respiratory cycles, or in which displacement may be induced with well-defined spatial and temporal characteristics and in a non-invasive and non-damaging manner, may be assessed using methods and systems of the present invention. Physiological conditions and/or biological responses, such as pain, may also be localized using methods and systems of the present invention. For example, tissue displacement and biological responses are induced by application of one or more acoustic beam(s) producing acoustic radiation force(s) or temperature change(s) or cavitation in tissue. Acoustic detection techniques that involve the application of acoustic interrogation signals to a target tissue site and acquisition of acoustic scatter data are preferred, but alternative detection techniques, including near-infrared spectroscopy (NIRS), magnetic resonance techniques, acoustic hydrophones and the like, may be used.

Methods and systems of the present invention are thus useful for assessing, localizing and monitoring various clinical parameters, and for diagnosing, localizing and monitoring various conditions, responses and disease states. These methods and systems are useful, for example, for non-invasively detecting tissue stiffness and compliance, and for assessing conditions that are related to tissue stiffness and compliance. The methods and systems are also useful, for example, for non-invasively probing targeted tissue sites, using focused ultrasound, to localize tissue responses, such as pain, that may be associated with damaged tissues or an underlying disease process. Targeted probing of internalized tissues by application of focused ultrasound provides highly sensitive localization of pain and may be used to diagnose numerous conditions producing pain, such as appendicitis, cholecystitis, pelvic inflammatory disease, pancreatitis, and lymphadenopathies, as well as to localize and identify the sources of pain in spine and other joints, as well as at other internal sites.

Thus, in one embodiment of the present invention, methods and systems employ noninvasive, focal ultrasound to differentially diagnose and localize pain by the focal, non-invasive and safe stimulation of individual potential sources of pain. Targeted acoustic probing of tissues is provided by the application of focused ultrasound pulses to the target tissue site. Application of an acoustic (ultrasound) pulse of an appropriate magnitude, frequency, intensity and/or pulse repetition rate to a target site that includes damaged tissue, for example, evokes the sensation of pain in a subject, while application of an ultrasound beam to tissue sites that are not damaged does not produce the sensation of pain. The level or type of pain may also be related to the magnitude, frequency, intensity and/or pulse repetition rate of the focused acoustic beam required to evoke the pain response.

Using the focused application of ultrasound beams, methods and systems of the present invention are employed to localize the source of a biological response, such as pain, within a generalized site of undifferentiated pain. Acoustic probing may involve discrete applications of focused ultrasound to produce discrete "pokes," or it may involve the application of acoustic energy to produce vibration or oscillation of tissues, as described by Greenleaf et al. (referenced above). Although one of the prime advantages of using focused acoustic probing to localize sources of pain is that a differential pain diagnosis is provided in an entirely non-invasive manner, the use of acoustic techniques to stimulate various biological responses, such as pain, may also be used in association with invasive or semi-invasive or minimally invasive apparatus and procedures, such as various types of diagnostic and surgical apparatus (e.g. endoscopes, and the like).

The technique of focused acoustic probing, described in detail below, may be combined with a diagnostic imaging technique, such as diagnostic ultrasound or magnetic resonance scanning techniques, to pinpoint the site of the acoustic probe(s) and, when a pain response is provoked, to pinpoint the source of the pain. When the subject is conscious, the subject's subjective sensation of pain may be used in combination with the imaging technique to pinpoint the source of pain as the focus of the acoustic probe is moved within the generalized site of pain. When the subject is not conscious or his pain responses have been dulled or blocked, other physiological responses or indicia of pain are used to identify the source of pain. Focused targeting of the ultrasound beam may be accomplished by selectively changing the position and/or focus of an acoustic transducer, for example, while localization of the focused acoustic beam and the source of the response may be provided by the associated imaging apparatus.

Focused acoustic probing of tissue sites to localize physiological conditions and responses, such as pain, may be employed for any tissue sites where a sufficient acoustic window is available for application and passage of a focused acoustic beam. Localization of generally undifferentiated pain in the abdomen and/or pelvic area provides for diagnosis of appendicitis, cholecystitis, pancreatitis, numerous gastro-intestinal conditions and disorders characterized by pain, gall stones, kidney stones, cystitis and various painful bladder conditions, dysmenorrhea, ovarian and uterine conditions, and the like. Generalized, undifferentiated pain in the area of the spine and in other joints, such as the knee, ankle, shoulder, hip, sacroiliac, and other joints, may be localized using the focused acoustic probing techniques of the present invention, and the source of pain may be identified, for example, as cartilage, muscle, nerve, ligaments, tendons, and the like. Using focused ultrasound to induce acoustic palpation, for example, back pain may be localized and identified as disc-related, or as originating in the facet, vertebral body, nerve, muscle or the like. Peripheral nerve-related pain and lymphadenopathies resulting, for example, from cancer and infections, may also be diagnosed and localized.

In many circumstances, a tissue site may not be terribly painful, but it may be enlarged or otherwise abnormal. Acoustic probing may be used to identify whether there are localized sites of pain within the enlarged or abnormal tissue site and thereby provide a positive diagnosis, or at least eliminate certain diagnoses. Enlarged tissue sites may result, for example, from tumors, other abnormal growths, inflamed tissue, or the like. Cancerous nodes are generally not painful, while enlarged nodes secondary to inflammatory conditions generally are painful. Thus, acoustic probing using the techniques described herein, provides a differential diagnosis of benign versus metastitic lymphadenopathy in patients with known head and neck primary tumors. This technique is also useful for providing a differential diagnosis in other anatomic locations, such as the mediastinum and the pelvis.

In another aspect, the methods and systems of the present invention are employed for non-invasively assessing CNS tissue properties and related clinical parameters, including ICP, and exemplary embodiments will be described with reference to non-invasive assessment of CNS tissue properties and ICP. Noninvasive methods and systems of the present invention are also useful for assessing arterial blood pressure (ABP) and cerebral perfusion pressure (CPP), and for assessing, diagnosing, localizing and monitoring CNS abnormalities and conditions such as acute, chronic and traumatic CNS damage and injury, vasospasm, stroke, local edema, infection, vasculitus, subdural and epidural hematomas, subarachnoid hemorrhages, ischemic conditions, multiple schlerosis, Alzheimers disease, hypoxic conditions, intracerebral hemorrhage, tumors and other intracranial masses, and the like. In other aspects, methods and systems of the present invention are used to assess, diagnose, localize and monitor abnormalities in other tissues, including heart tissue, peripheral nerves, and other non-bony tissues. In some cases, assessments are made independent of comparison to a comparative tissue sample, while in other cases, assessments are made by comparison of properties at various target tissue sites. In some embodiments, measured tissue properties are compared to empirically determined standards.

One aspect of methods and systems of the present invention relates to assessment and monitoring of various clinical parameters, including ICP, as a function of properties of CNS tissue that are related to intrinsic and/or induced tissue displacements, or associated biological responses, at target tissue sites. "Normal" brain tissue is compliant and elastic. The brain rests within a pool of cerebral spinal fluid (CSF) and is protected by the closed cranial vault. With each cardiac cycle, a bolus of arterial blood enters and venous blood exits brain parenchyma, causing that tissue to expand and contract during the cardiac cycle in a way that is modulated by respiration. The net volume of blood within the brain at any time point within the cardiac cycle is a function of systemic blood pressure and the protective autoregulatory mechanisms of the brain vasculature. During the cyclical contraction and expansion of the brain, blood flow to the brain is maintained and the cerebral vasculature dynamically adjusts its resistance to compensate for changes in mean arterial blood pressure.

ICP and autoregulation status are essential clinical parameters that are difficult to measure and even more difficult to monitor using available clinical techniques. FIG. 1A shows a typical ICP waveform measured by traditional, invasive means. The ICP curve is superimposed on the respiratory cycle and arterial blood pressure wave form. FIG. 1B shows an enlarged view of the waveform enclosed by the box in FIG. 1A, showing the canonical shape of the waveform resulting from the elements of the cardiac cycle and the autoregulation system. The shape of the CSF pressure wave is similar to that of systemic blood pressure. It has three fairly consistent components, the "percussion wave" (P1), the "tidal wave" (P2), and the "dicrotic wave" (P3). The dicrotic notch between P2 and P3 corresponds to the dicrotic notch of the arterial pulsation.

The respiratory wave is synchronous with alterations in central venous pressure, reflecting intra-thoracic pressure. Specifically, during inhalation, intra-thoracic pressure decreases as the chest cavity expands, as does ABP; hence, ICP decreases. During exhalation, intra-thoracic pressure increases as the volume of the chest cavity decreases, ABP increases; hence, ICP increases. The opposite holds true for subjects whose respiration is assisted by a mechanical ventilator. Adjustments to intra-thoracic pressure using a mechanical ventilator may be used, to some degree, to regulate ABP and ICP. Normally, the amplitude of the cardiac pulse is about 1.1 mmHg, and the combined cardiac and respiratory variation is approximately 3.3 mmHg.

Brain tissue, and other CNS tissue, including, e.g., CSF, tissue adjacent to CSF or brain parenchyma, cranial nerves such as the optic nerve, and the like, are suitable target tissue sites for assessment of ICP. Elevated ICP causes brain and other CNS tissue to become relatively stiffer, or less compliant, when subjected to forces, such as intrinsic forces, exerted on the CNS tissue as a consequence of respiration, cyclic blood flow, compensating CSF and venous outflow, and autoregulatory-based changes in the cerebral vasculature, or when subjected to extrinsic (induced) forces exerted on the CNS tissue. The properties of blood vessels change—i.e. the vessel walls become stiffer or more pliable—as the tissue compresses or expands, or during vasoconstriction or vasodilation, respectively, producing, for example, local manifestations of the pulsatility of the cerebral vasculature.

The inventors have established that the stiffness of CNS tissue, particularly brain tissue and optic nerve tissue, may be assessed by observing acoustic properties of CNS tissue that relate to intrinsic and/or induced CNS tissue displacement, or associated biological responses. Associated biological responses include, but are not limited to, changes in local perfusion rate, blood-flow velocity, and electrophysiological activity. The acoustic properties of tissue, tissue stiffness, intrinsic and/or induced tissue displacements and associated biological responses, are empirically related to ICP and other CNS conditions.

Although evaluation of acoustic properties of tissue is a preferred embodiment for methods and systems of the present invention, parameters relating to intrinsic and/or induced tissue displacement and associated biological response(s) used for the assessment of tissue properties such as tissue stiffness or compliance, may be measured using other non-invasive techniques, including non-invasive optical detection techniques, such as near infrared spectroscopic (NIRS) techniques, optical coherence tomography (OCT), magnetic resonance techniques, positron-emission tomography (PET), external electrophysiological stimulation, and the like. A portable, relatively low-cost magnetic resonance scanner is described, for example, in the California Institute of Technology Engineering and Science publication, Vol. LXIV, No. 2, 2001. The use of these techniques to measure various spatial and temporal aspects of tissue displacement and associated biological responses is generally known.

Ultrasound detection techniques are preferred for many embodiments. Ultrasound sources and detectors may be employed in a transmission mode, or in a variety of reflection or scatter modes, including modes that examine the transference of pressure waves into shear waves, and vice versa. Ultrasound detection techniques may also be used to monitor the acoustic emission(s) from insonified tissue. Detection techniques involving measurement of changes in acoustic scatter, particularly backscatter, or changes in acoustic emission, are particularly preferred for use in methods and systems of the present invention. Exemplary acoustic scatter or emission data that are related to tissue properties include: changes in scatter or acoustic emission, including changes in the amplitude of acoustic signals, changes in phase of acoustic signals, changes in frequency of acoustic signals, changes in length of scattered or emitted signals relative to the interrogation signal, changes in the primary and/or other maxima and/or minima amplitudes of an acoustic signal within a cardiac and/or respiratory cycle; the ratio of the maximum and/or minimum amplitude to that of the mean or variance or distribution of subsequent oscillations within a cardiac cycle, changes in temporal or spatial variance of scattered or emitted signals at different times in the same location and/or at the same time in different locations, all possible rates of change of endogenous brain tissue displacement or relaxation, such as the velocity or acceleration of displacement, and the like. Multiple acoustic interrogation signals may be employed, at the same or different frequencies, pulse lengths, pulse repetition frequencies, intensities, and the multiple interrogation signals may be sent from the same location or multiple locations simultaneously and/or sequentially. Scatter or emission from single or multiple interrogation signals may be detected at single or at multiple frequencies, at single or multiple times, and at single or multiple locations.

Acoustic scatter and/or emission data from selected target tissue site(s), or derivative determinations such as tissue displacement, tissue stiffness, and the like, are related, using empirical formulations and/or mathematical models, to a useful tissue property or clinical parameter, such as ICP. In general, higher tissue stiffness and/or lower compliance indicates a higher relative ICP, while lower tissue stiffness and/or higher compliance indicates a relatively lower ICP. Similarly, localized differences and/or changes in acoustic scatter and/or emission that are related to tissue stiffness properties are indicative of localized conditions such as vasospasm, ischemic or hypoxic conditions, tumors or other masses, or the presence or progression of various disease states, such as Alzheimer's disease, multiple sclerosis, and the like. Supplemental data, such as noninvasive measures of mean and/or continuous arterial blood pressure and tracking of the cardiac and/or respiratory cycles, may be used in combination with acoustic data to assess ICP and other clinical parameters or tissue conditions.

In both "active" and "passive" modes, single or multiple interrogation signals administered from different places and/or at different times may insonify single or multiple target tissue sites. Acoustic properties of the insonated target tissue may be assessed, by acquiring scatter or emission data, simultaneously and/or sequentially, to evaluate intrinsic and/or induced tissue displacement, or associated biological responses. In some embodiments, the absolute values for intrinsic and/or induced tissue displacement may be useful, while in other embodiments, intrinsic and/or induced tissue displacement determinations are evaluated by comparison of acquired data to empirically determined standards, by comparison to data acquired from different target tissue sites at the same or different time points, and/or by comparison to data acquired from target tissue sites over time. Active and passive modes may be used separately, or in combination, to assess target tissues.

Tissue target sites may be volumetrically large and provide data relating to large areas for gross assessment of CNS tissue properties. One of the advantages of the methods and systems of the present invention, however, is that target tissue sites may be volumetrically small, and spatially resolved, to provide data from localized tissue sites with a high degree of spatial resolution. In this way, localized differences in tissue properties may be identified and associated with a spatial location within the interrogated tissue. According to one embodiment, tissue sites of varying size and/or location are assessed simultaneously or sequentially. For most applications, the use of acoustic source(s) and./or transducer(s) capable of interrogating and detecting target tissue sites having a volume of from 1 $mm^3$ to 100 $cm^3$ are suitable.

For assessment and/or monitoring of CNS tissue properties, such as ICP, based on the acoustic properties of tissue in an "active" and/or "passive" mode, the target tissue site is preferably brain tissue or other CNS tissue, such as optic nerve or optic disc tissue. The stiffness and/or compliance of brain, optic nerve and optic disc tissue, as determined by acquisition and processing of acoustic scatter and/or emission data during the course of the cardiac and respiratory cycles, is related to ICP. For some applications, the CNS target tissue site is selected based on the homogeneity of the tissue sample, while for other applications, the target tissue site is selected based on the known or predicted variation of tissue types within the target site.

For assessment of CNS properties in a passive mode and absent ABP data, non-ventricular CNS target sites are generally preferred. Ventricular target tissue sites, such as sites in the CNS at or in proximity to a fluid storage site such as the ventricles, the choroid plexus, the spinal column, and the like, may be suitable target tissue sites when ABP data is used in combination with acoustic data relating to intrinsic and/or induced tissue displacement to assess clinically important parameters. Also, in an active or a combined active/passive mode of operation, ventricular target tissue sites are suitable. One or more CNS target tissue sites may be monitored simultaneously or sequentially and may contribute to the assessment.

Local differences in ICP or ABP, or various tissue properties, may be assessed by acquiring acoustic scatter or acoustic emission data relating to intrinsic and/or induced tissue displacements, or associated biological responses, from multiple sites simultaneously or sequentially. The ability to localize tissue sites having different ICP or ABP properties, and different tissue properties, is useful for localizing ICP and ABP abnormalities, vascular abnormalities indicative of vasospasm, stroke, hypoxic or ischemic conditions, subdural and epidural hemotomas, intracerebral hemorrhage, infection, vasculitis, and the like. The ability to localize tissue sites having different tissue stiffness properties is useful for localizing and identifying tissue having "abnormal" compliance properties, and may be used to diagnose and monitor conditions such as Alzheimer's disease, multiple sclerosis, tumors and other intra-cranial masses, and the like.

Assessment and monitoring of CNS target tissue sites using the "active" and/or "passive" acoustic systems of the present invention also provide a measure of the status and condition of the cerebral vasculature. Vasospasm, for example, is an important clinical parameter that is traditionally assessed using transcranial Doppler (TCD) sonography to examine the flow velocities in large cerebral vessels. If the velocity of blood flow within the blood vessel of interest exceeds a certain value, vasospasm is inferred. Smaller cerebral blood vessels, which may also undergo vasospasm, generally cannot be accurately localized using TCD techniques. Using methods and systems of the present invention to assess CNS (e.g. brain) tissue displacement, changes in the pulsatilty of the tissue in selected target tissue sites may be assessed to spatially locate and identify tissue that is in a condition of vasospasm. Using these methods and systems, vasospasm may be assessed throughout the brain, and not only in the large blood vessels at the base of the skull. Similarly, assessment of changes in CNS tissue characteristics of the brain, measured by ultrasound and using techniques described herein, permits determination of the onset and monitoring of the degree of severity and progression of various pathological conditions, such as stroke, local edema, infection, and vasculitis.

In yet another aspect, methods and systems of the present invention may be used to non-invasively determine the autoregulation status of a patient together with, or separately from, a determination of ICP, ABP, CPP and other CNS tissue properties. The non-invasive methods and systems of the present invention for assessing intrinsic or extrinsic CNS tissue displacements over the course of the cardiac and/or respiratory cycle(s), as described above, may be substituted for the more conventional, invasive methods and systems for assessing ICP, CPP and/or autoregulation in conventional approaches to assessing the autoregulation status or capacity of a patient. The intrinsic or extrinsic tissue displacement data may be supplemented with data relating to mean and/or continuous arterial blood pressure to assess autoregulation status or capacity, as described in greater detail below. And, challenges resulting in a modulation of the arterial blood pressure administered, for example, by having a subject perform actions that change the ABP in a predictable fashion, by adjusting intra-thoracic pressure using a ventilator, by restricting blood flow to an extremity, or by administering an agent, such as a diuretic and/or vasodilator or vasoconstrictor, that modulates arterial blood flow, may be used with methods and systems of the present invention to assess autoregulation.

In yet another aspect, noninvasive systems and methods of the present invention provide a measure of arterial or venous blood pressure using acoustic techniques to measure alternating compression and dilation of the cross-section or other geometric or material properties of an artery or vein, using empirically established relationships and/or mathematical models. In another aspect, blood pressure is determined using acoustic techniques to measure alternating compression and dilation of tissue surrounding blood vessels that is displaced as the vessels are compressed and dilated with the cardiac cycle. Geometrical properties that may be determined using acoustic detection techniques include changes in diameter, cross-sectional area, aspect ratio, rates of changes in diameter, velocity, and the like. Material properties that may be determined using acoustic detection techniques include the stiffness of vessel walls or tissue in proximity to vessel walls. Blood pressure may be assessed, for example, by acquiring acoustic data, in an active and/or passive mode, from target tissue sites at or in proximity to one or more blood vessels. The acoustic data can be related to the stiffness of vessel walls or supporting tissue, which can be related to blood pressure, just as acoustic data from a CNS target tissue site can be related to tissue stiffness, which can be related to ICP. Suitable target tissue sites for determination of arterial or venous blood pressure may comprise any blood vessel or surrounding tissue. Detection of ultrasound scatter data may be related, for example, with synchronous Doppler flow measurements within the same vessel.

A calibration step using a measure of blood pressure taken with a conventional blood pressure device, may be incorporated in the blood pressure determination. Acoustic proxies for the pulsatility of the blood vessel—such as oscillation rate of the blood vessel wall—may be substituted for direct measures of those quantities. In this method, the spontaneous changes in the diameter (or other geometric property) of the vessel being monitored are assessed using ultrasound, and this information is related (e.g., using correlation techniques) to synchronous Doppler flow measurements within the same vessel. Since the diameter (or other geometric property) of the vessel is a function of the pressure being exerted against the wall of the vessel by blood, and since the velocity of blood flow is dependent on the diameter (or radius) of the vessel through which the blood travels, blood pressure can be calculated from flow velocity measured by Doppler. By simultaneously measuring the pulsatility of the blood vessel of interest and the Doppler flow velocity proximal and distal to this site, continuous blood pressure can be determined.

In one embodiment, described in detail below, an acoustic detector, such as an ultrasound transducer, detects ultrasound signals that are indicative of tissue displacements, or associated biological responses, in one or more of the following operating modes: transmission, reflection, scatter, emission, backscatter, echo, Doppler, color Doppler, harmonic, subharmonic or superharmonic imaging, a-mode, m-mode, or b-mode. Ultrasonic interrogation pulses having a known frequency, intensity and pulse repetition rate are administered to a desired target tissue site. The intensity, frequency and pulse repetition rates of the ultrasonic interrogation pulses are selected such that the interrogation pulses do not produce undesired side effects, and do not substantially interfere with intrinsic tissue displacements resulting, for example, from blood flow and respiration. Transmitted signals, signal reflections, acoustic emissions, scatter such as backscatter, and/or echoes of the interrogation pulses are detected and used to assess intrinsic tissue displacements and/or tissue properties at the target tissue site. In preferred embodiments of the passive assessment mode, an acoustic detector is implemented to detect the backscatter of administered interrogation signals. An acoustic detector may additionally or alternatively be operated in a Doppler mode to measure the phase shift of ultrasound reflected back to the detector.

A variety of techniques may be used to analyze the acquired acoustic data relating to intrinsic and/or induced CNS tissue displacement or associated biological responses. For example, analytical techniques developed and employed in connection with ultrasound imaging, such as cross-correlation, auto-correlation, wavelet analysis, Fourier analysis, CW Doppler, sum absolute difference, and the like, may be employed to determine various properties of tissue deformation, and to relate tissue deformation to tissue properties. False peak correction techniques may be used to improve the accuracy of the assessment. Additionally, properties of the major and minor endogenous oscillations of brain tissue within a cardiac cycle, or relationships between major and minor endogenous oscillations within a cardiac cycle, or across several respiratory cycles, are empirically related to ICP and other tissue properties and conditions. These determinations may be made with, or without, additional information relating to ABP and/or respiration and/or exogenous tissue displacements.

Methods and systems of the present invention are preferably integrated with control and data storage and manipulation features similar to the control and data storage and manipulation features provided on other types of diagnostic and monitoring systems. Various types of control features, data storage features, data processing features, data output features, and the like, are well known in the art and may be adapted for use with the present invention.

Various modes of operation of methods and systems of the present invention are described below and in the description of preferred embodiments.

"Passive" Acoustic Mode

In a "passive" acoustic mode, methods and systems of the present invention employ acoustic techniques, such as ultrasound, to acquire data relating to intrinsic (endogenous) tissue displacements. Ultrasound backscatter and/or emission data, for example, are related to intrinsic tissue displacements, which can be related to ICP, ABP, CPP and various tissue properties indicative of conditions such as vasospasm, stroke, local edema, infection and vasculitis, as well as Alzheimer's disease, multiple sclerosis, ischemic conditions, hypoxic conditions, subdural and epidural hematomas, subarachnoid hemorrhage, intracerebral hemorrhage, tumors and other intra-cranial masses, and the like. Acoustic scatter measurements may also be used to assess the autoregulation status, or capacity, of CNS tissue. Supplemental data, such as measures of mean and/or continuous arterial blood pressure, blood flow, and the like, may additionally be used in these determinations.

For example, the magnitude or amplitude or phase of acoustic scatter from target tissue sites in the CNS undergoing intrinsic displacements during the course of arterial blood flow and CSF supply, is directly related to the stiffness, e.g. Young's modulus, of the CNS tissue, and is therefore empirically related to ICP. Alternatively or additionally, relationships between the major and minor intrinsic oscillations of CNS tissue within a cardiac cycle, or within a cardiac cycle as modulated by one or more respiratory cycles, are empirically related to ICP. Additional properties of the intrinsic tissue displacement that may be determined and related to tissue properties include: various components of amplitude, such as maximum amplitude within a cardiac cycle, the ratio of the maximum amplitude to that of the mean or variance of subsequent oscillations within a cardiac cycle, all possible rates of change of intrinsic CNS tissue displacement or relaxation, such as the velocity or acceleration of displacement, and the like. Additional data, such as ABP measurements and/or respiration data, may be collected and used, with the acoustic data, to make various assessments and determinations of ICP, CPP, autoregulation status or capacity, and the like.

First "Active" Acoustic Probing or Palpation Mode

In a first "active" mode, methods and systems of the present invention stimulate or probe target tissue, or induce a response at a target tissue site, by application of focused ultrasound. The response of the targeted tissue to the application of focused ultrasound may be displacement or a change in relative position, a sensation such as pain, a change in temperature, a change in blood flow, or another detectable response. For example, application of an acoustic radiation force to "palpate" a target tissue location may be accomplished by administering one or more acoustic signals. Non-invasive techniques, such as ultrasound, optical techniques such as near infrared spectroscopy and optical coherence tomography, and other techniques, including magnetic resonance techniques, external electrophysiological stimulation, patient response, and the like are used to assess at least one response to the application of focused ultrasound. A visualization or imaging technique, such as ultrasound imaging or magnetic resonance imaging, may also be employed to assist in targeting the focused ultrasound pulse(s) and to assist in differentially localizing responsive tissues.

Acoustic techniques, such as ultrasound, may be used to induce biological responses in tissue, such as pain, and to deflect or deform biological materials. Davies et al. have shown, for example, that short pulses of focused ultrasound stimulate the superficial and deep-seated receptor structures of human tissues and induce different somatosensory sensations including, in particular, pain sensations. Davies et al., *Application of focused ultrasound for research on pain*, Pain, 67:17–27 (1996)—1996 International Association for the Study of Pain.

Biological materials, such as CNS tissue, absorb some of the ultrasound as it propagates into and through the material. See, e.g., Rudenko et al. (1996), "Acoustic radiation force and streaming induced by focused nonlinear ultrasound in a dissipative medium," J. Acoust. Soc. Am 99(5) 2791–2798.

Also, at the boundaries between different tissue types, such as between CSF and brain tissue, there is an 'impedance mismatch' (that is, differences between the product of density and speed of sound from one tissue to another) that allows ultrasound to push on the interface. See, e.g., Chu and Apfel (1982) "Acoustic radiation pressure produced by a beam of sound," J. Acoust. Soc. Am 72(6), 1673–1687. The deflection caused by the radiation force described by Chu is likely greater for brain than that of radiation force described by Rudenko et al., either at the CSF/brain interface for ultrasound with a wavelength significantly smaller than the distance between dura and brain, or at the effective bone/brain interface for ultrasound with a wavelength significantly larger than the distance between dura and brain. The formula for the two contributions to radiation pressure can be modified for wavelengths of sound comparable to the distance between dura and brain.

In the described embodiments, we have made certain simplifying assumptions, just described, without limiting the scope of the application. It is useful to note the following formula for the net pressure (force per unit area) P at an interface between two tissues given by Chu and Apfel, their equation (69):

$$P=2(\rho_1/\rho_0)*K*<E>*(1+(\rho_1 c_1)/(\rho_0 c_0)^{-2})$$

where $\rho_i$ is the density of the medium (i), $c_i$ is its sound speed, K is the "nonlinearity" parameter of medium 1, and $<E>$ is the time-averaged energy density associated with the ultrasonic wave incident on the target site, which can be calculated if one knows the amplitude of the acoustic wave at the interface of interest. For present purposes, medium "1" is the brain, while medium "0" is either the CSF or bone.

Tissue displacement may thus be induced, and tissue may be acoustically palpated or oscillated, to produce displacement and other biological responses, and acoustic emissions, by application of focused ultrasound. Using an acoustic radiation force, a single frequency acoustic source causes materials that are at least somewhat compliant, such as brain tissue, to move in a single direction relative to the source during propagation, while the material returns to its original location when propagation from the acoustic source is discontinued. Repeated pulses induce a repeated series of displacements and relaxations of the tissue.

For assessment of CNS tissue and determination of ICP, for example, one or more acoustic transducer(s) is placed in contact with or in proximity to a subject's skull. An initial environmental assessment, described below and preferably employing ultrasound techniques, may be made, if desired, to assess the characteristics of the environment between the acoustic source and the target tissue site, so that the magnitude of the acoustic force applied to the target tissue may be determined. Environmental factors, such as the distance between the acoustic transducer and various structural landmarks, such as the brain surface, the thickness of the skull, the thickness of the dura matter, the thickness of the arachnoid layer containing CSF, impedance mismatches between the various structures and tissues, and the like, may be determined. The initial environmental assessment is determinative of various method and system parameters. Environmental assessments may additionally be updated at intervals throughout a diagnostic or monitoring procedure.

Following the environmental assessment, an acoustic force is applied by an acoustic transducer, at a predetermined frequency, to displace the brain tissue at a desired location, such as at the surface of the brain. The deformation may be produced at any desired location within tissue, depending on the focus (foci) of the ultrasonic transducer(s) producing the acoustic radiation force. In some systems, variable foci ultrasonic transducers are provided, and a diagnostic procedure is carried out using a plurality of target tissue sites. According to one embodiment for assessment of ICP, the focus (foci) of the ultrasonic transducer(s) is preferably provided in proximity to the cortical surface or a small distance below the cortical surface, to maximize the tissue displacement induced by the radiation pressure that arises from the impedance mismatch between brain and CSF or between brain and bone (depending on the frequency of the applied ultrasound). It is important to note, again, that the methods and systems of the present invention do not require the radiation force arising from the impedance mismatch described by Chu and Apfel to be significantly greater than that described by Rudenko et al.

The applied acoustic radiation force is sufficient to induce a detectable displacement in the CNS tissue, or the applied ultrasound beam is sufficient to produce a detectable biological response, without producing any medically undesirable changes in the examined tissue. For example, the acoustic radiation force applied must not produce shear in tissues in proximity to the target tissue of a magnitude sufficient to tear or damage tissue. The applied ultrasound, moreover, must not appreciably increase the temperature of examined tissue to the point of causing unacceptable damage, and it must not induce extensive or damaging cavitation or other sources of deleterious mechanical effects in the examined tissue. Suitable ultrasound dosages may be determined using well known techniques. For example, Fry et al. studied the threshold ultrasonic dosages causing structural changes in mammalian brain tissue and illustrate, in their FIG. 1, the acoustic intensity v. single-pulse time duration producing threshold lesions in white matter of the mammalian (cat) brain. Fry et al., *Threshold Ultrasonic Dosages for Structural Changes in the Mammalian Brain*, The Journal of the Acoustical Society of America, Vol. 48, No. 6 (Part 2), p. 1413–1417 (1970).

Additionally, the acoustic frequency must be low enough to penetrate the skull and high enough to produce measurable deformation in the target tissue at the location of interest. Within the parameters outlined above, higher frequency acoustic waves are more easily focused and, therefore, preferred. The intensity must be high enough to deform the tissue, but not be so great as to induce undesirable changes in the examined tissue. The pulse length is preferably relatively short, but long enough to create a measurable deformation or oscillation of the target tissue, as desired, while the pulse repetition frequency must be large enough to resolve medically interesting temporal features in the tissue, without inducing medically unacceptable changes in the tissue.

In general, at least one acoustic property related to tissue displacement, or an associated biological response, is determined and related to a tissue property and, ultimately, to a clinically important parameter. For example, the magnitude, or amplitude, of the displacement induced by the known acoustic force is directly related to the elasticity (or stiffness or compliance, e.g., Young's modulus) of the CNS tissue, and can therefore be empirically related to ICP. Additional properties of the target tissue displacement that may be determined and related to tissue properties include: various components of amplitude, such as maximum amplitude in the direction of the acoustic force or maximum amplitude perpendicular to the direction of acoustic force; all possible rates of change of the displacement or subsequent relaxation of the tissue, such as the velocity or acceleration of displacement or relaxation; the amplitude or rates of change of various components of the shape of the displacement; changes in Fourier or wavelett representations of the acoustic scatter signal associated with the displacement; properties of shear waves generated by the acoustic radiation force; properties of induced second harmonic deformation(s), and the like. Time displacements of pulse echoes returning from the target tissue are also indicative of the displacement amplitude and may be determined. These properties are all referred to as measures of "displacement."

Second "Active" Acoustic Probing or Palpation Mode

In a second "active" mode of operation, application of focused ultrasound produces oscillation of targeted tissue, and data relating to the acoustic signals emitted from the targeted tissue are collected. These signals are referred to herein as acoustic emissions. In general, methods and systems of the present invention that relate to application of focused ultrasound may be used to produce oscillation of targeted tissue, and emitted acoustic signals are related to tissue properties and physiological conditions.

In one embodiment, methods and systems of the present invention employ a confocal acoustic system comprising at least two acoustic transducers, driven at different frequencies, or a focal acoustic system comprising a single acoustic transducer driven at a given pulse repetition frequency (PRF), to induce an oscillatory radiation force in the target tissue, such as brain tissue. The resulting oscillation is at a frequency that is the difference of the applied frequencies, at the target location that is marked by the overlap of the two confocal acoustic beams or, for the single transducer case, at the PRF. During and after the application of focused ultrasound, the targeted tissue emits acoustic signals related to its intrinsic properties. The second, active mode of operation may therefore be used to characterize tissue. Diagnostic ultrasound techniques may be used to measure the frequency or other properties of the emitted acoustic signal, which are empirically related to tissue properties.

BRIEF DESCRIPTION OF THE FIGURES

FIG. 2 is a schematic diagram illustrating a system of the present invention for inducing and detecting tissue deformation for assessing tissue properties and ICP.

FIG. 5A is a schematic diagram illustrating an undisplaced target brain surface, and FIG. 5D shows an acoustic scatter signal characteristic of undisplaced brain tissue acquired at time t.

FIG. 5B is a schematic diagram illustrating deflection of target brain tissue during application of an acoustic radiation force, and FIG. 5E shows an acoustic scatter signal resulting from the deflection of the brain tissue displaced a time interval Δt from the acoustic scatter signal of FIG. 5D.

FIG. 5C is a schematic diagram illustrating the relaxation of the target brain surface following application of the acoustic radiation force, and FIG. 5F shows an acoustic scatter signal characteristic of the relaxed brain tissue, acquired at time t, which is substantially the same signal and time as the undisplaced brain tissue.

FIG. 8A shows an exemplary ICP output display;

FIG. 8B shows an exemplary ABP output display; and

FIG. 8C shows an exemplary autoregulation status output display.

DETAILED DESCRIPTION OF THE INVENTION

Figure 1A:
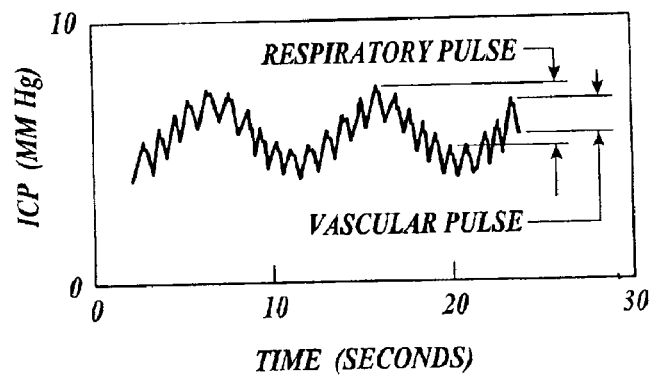
FIG. 1A shows a typical ICP waveform as measured by traditional, invasive techniques.

While the methods and systems of the present invention may be embodied in a variety of different forms, the specific embodiments shown in the figures and described herein are presented with the understanding that the present disclosure is to be considered exemplary of the principles of the invention, and is not intended to limit the invention to the illustrations and description provided herein. In particular, preferred embodiments of methods and systems of the present invention are described with reference to assessment of brain tissue and ICP. It will be recognized by those having skill in the art that the methods and systems of the present invention may be applied to other mammalian tissue targets and, more broadly, to other types of material targets.

Several exemplary systems of the present invention for acquiring data indicative of intrinsic and/or induced tissue displacements are described below. Although such systems may utilize commercially available components, the processing of the acquired data and the correlation of the acquired data to medically relevant physiological properties provides new modalities for noninvasively assessing numerous physiological parameters. Exemplary data processing techniques for detecting intrinsic and/or induced tissue displacements using acquired acoustic scatter or emission data and relating the acoustic scatter or emission data, or the displacement data, with clinically important parameters, such as ICP, ABP autoregulation status, and source of pain, are also disclosed below. These techniques are exemplary and methods and systems of the present invention are not intended to be limited to the use of these exemplary techniques.

In a simplified system (not illustrated), a single acoustic transducer may provide the interrogation signal(s) required for tissue assessment in passive modes, the acoustic force required for tissue displacement in active modes, and additionally may provide for detection of scattered interrogation signal(s) that are indicative of intrinsic (passive mode) or induced (active mode) tissue displacement. For example, commercially available ultrasound transducers have sufficient bandwidth, such that a single transducer may be used to emit interrogation signal(s) for measuring intrinsic tissue displacements when operating at a first frequency, a first pulse repetition rate and a first intensity; to induce (exogenous) displacement or oscillation of tissue when operating at a second frequency, a second pulse repetition rate and a second intensity, and to detect signals reflected or backscattered or echoed or emitted from the tissue, e.g. when operated at a third frequency, or at additional frequencies, to assess the intrinsic or induced tissue displacement or emission, or to assess a biological response to the intrinsic or induced tissue displacement. Multiple acoustic transducers may also be used. In another embodiment, one or more diagnostic ultrasound probes and one or more displacement ultrasound probes may be embodied in a single acoustic element.

In general, acoustic interrogation pulses have larger peak positive pressure, have a higher frequency, and are shorter than acoustic palpation pulses. Acoustic interrogation pulses, for example, may have a typical frequency between 0.5 and 15 MHz, use from 1–50 cycles per pulse, consist of 3–10,000 pulses per second, and have a time-averaged intensity of less than 0.5 W/cm$^2$. Acoustic palpation signals may, for example, have a frequency of from 0.5 to 10 MHz, consist of long tone bursts of from 0.1–100 ms, consist of 1–100 pulses per second, and have a time averaged intensity of less than 100–1000 W/cm$^2$, where longer pulses have lower intensities, for example. Acoustic emissions from palpated or oscillated tissue are expected to be in the frequency range of 500 Hz to 10 KHz.

FIG. 2 is a schematic diagram illustrating a system of the present invention for inducing and/or detecting at least one aspect of intrinsic or induced tissue displacement for applications such as assessment of tissue properties and ICP. As shown in FIG. 2, systems of the present invention comprise an acoustic source and receiver combination 10 for non-invasively assessing tissue displacement or emission at a distance from the source/receiver combination. In one embodiment suitable for use in passive modes to assess intrinsic tissue displacement, acoustic source and receiver combination 10 comprises one or more acoustic source(s) 22 for producing an interrogation signal. In another embodiment suitable for use in active modes to assess induced tissue displacement or emission, acoustic source and receiver combination 10 comprises one or more acoustic source(s) 12 for generating an acoustic radiation force, or for generating an oscillatory radiation force, or inducing an acoustic emission. Acoustic source(s) 12 are driven by and operably connected to an amplifier or power source 14, which is operably connected to one or more function generator(s) 16, which is operably connected to a controller 20. Controller 20 preferably has the capability of data acquisition, storage and analysis.

Controller 20, function generator 16 and amplifier 14 drive acoustic source(s) 12 in an interrogation (passive) or an acoustic radiation force (active) mode. In the passive mode, controller 30, function generator 28 and amplifier 26 drive acoustic source(s) 22 through the diplexer 24 at a desired frequency, intensity and pulse repetition rate to produce an interrogation signal for tissue target 32, such as CNS tissue, without producing undesired side effects, and without producing a significant (exogenous) displacement. The resulting scattered signal is received at controller 30 via diplexer 24. In the active mode, controller 20, function generator 16 and amplifier 14 drive acoustic source(s) 12 at a desired frequency, intensity and pulse repetition rate to produce a displacement in tissue target 32, such as CNS tissue, without producing undesired side effects. In some embodiments, the controllers 20 and 30 communicate with one another to interleave their signals in time, for example. The system based on transducer 22 can monitor the displacements and/or emissions induced by transducer 12.

The operating acoustic parameters are related to one another and suitable operating parameters may be determined with routine experimentation. The focal point of the acoustic source(s), or transducer(s), may be fixed and non-adjustable as a consequence of the mechanical configuration of the transducer. Alternatively, multiple transducers may be provided and arranged to permit variation and adjustment of the focal point. Acoustic sources, or transducers, are preferably annular in configuration and, in preferred embodiment, acoustic source 12 comprises multiple annular transducers arranged in a concentric configuration. Acoustic sources and tranducers may be arranged axially or off-axis with respect to one another, with their foci overlapping or not.

A second acoustic source 13 driven by and operably connected to a diplexer 15, which is operably connected to an amplifier or power source 17, which is operably connected to a function generator 19, which, in turn, communicates with controller 20 and/or controller 30 may also be provided, as shown in FIG. 2. Acoustic source 13 may be used for assessing the characteristics of the environment between the acoustic source(s) and the target tissue, and may operate independently of transducer 12 and the related driver and controller components used for the assessment of the target tissue, or in coordination with transducer 12.

Figure 3:
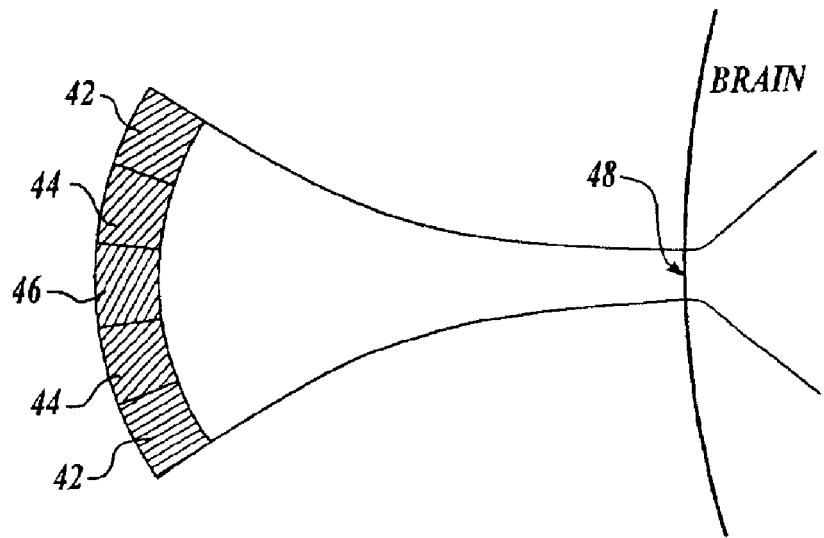
FIG. 3 is a schematic diagram illustrating another system of the present invention for inducing and detecting tissue deformation for assessing tissue properties and ICP.

FIG. 3 illustrates one embodiment of an acoustic source and probe combination 40 that is especially suitable for use with the active mode of tissue assessment of the present invention. Source and probe combination 40 comprises confocal, annular acoustic sources 42 and 44 and a diagnostic ultrasound probe 46. Phasing acoustic sources 42 and 44 at slightly different frequencies produces a significant radiation force only at their mutual focus, indicated in the brain, such as near the brain surface at location 48, and deforms the tissue. When a single acoustic source is used, or the sources are used such that there is no difference in frequency between the sources, the result is a unidirectional displacement of the brain at a target that coincides with their overlapping foci, with negligible oscillatory component for the duration of each acoustic pulse. Under these circumstances, repeated single-frequency pulses will create periodic pulsations of the tissue at the frequency of the PRF. In either embodiment, acoustic emissions may be generated from the transiently deformed tissue, with the emissions monitored by transducer 46 and related to tissue properties or physiological conditions. Alternatively, the displacements may be monitored by transducer 46 and related to tissue properties or physiological conditions.

The acoustic source and probe combination 40 illustrated in FIG. 3 may also be used, in combination with an imaging system, to acoustically palpate tissue at targeted sites to localize tissue responses to the focused ultrasound, such as pain. The imaging system may employ ultrasound or another tissue imaging modality, such as magnetic resonance imaging, computed tomography, fluoroscopy, or the like. Using an acoustic source with a probe combination having ultrasound imaging capability, for example, provides visualization of the target site and aids targeting of the acoustic radiation force and localization of responses, such as pain. Pain responses may generally be subjectively reported by a subject.

Figure 4:
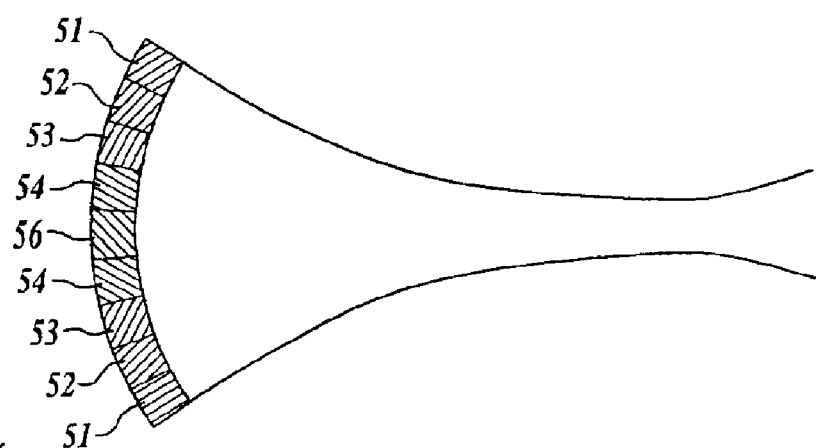
FIG. 4 is a schematic cross-sectional diagram illustrating the use of confocal acoustic sources to produce tissue displacement and a diagnostic ultrasound probe to measure the amplitude of the displacement.

FIG. 4 illustrates another acoustic source and probe combination 50 comprising a plurality of ultrasonic transducers 51, 52, 53 and 54, arranged as concentric annular elements. Each annular acoustic source represents a single frequency source of ultrasound that cooperates, with the other acoustic sources, to interrogate and/or displace tissue at a selected location. The foci of the annular transducers may be the focus of the interrogation signal, or the radiation force, and the location of assessment of intrinsic tissue displacement and/or induced tissue displacement and/or emissions. More or fewer ultrasonic transducers may be used. A larger number of annular transducers generally provide a greater degree of control and precision of where the interrogation signals, or the radiation force, is focused. This arrangement of annular transducers may also be used, in a variable frequency mode, to generate an oscillatory radiation force in target tissue. When multiple acoustic sources are used, each source is operated by a controller, amplifier and function generator, but operation of the separate acoustic sources is controllable using a centralized control system. This acoustic system may be further generalized or modified for specific applications by using a non-annular or non-axial distribution of transducers to allow for additional ultrasound beam forming or electronic steering.

Detection element 56 is provided in acoustic combination 50 to detect at least one aspect of intrinsic and/or induced tissue displacement. In one embodiment, element 56 comprises a diagnostic ultrasonic probe that emits an ultrasonic pulse toward the site of tissue displacement and detects its echo to track the magnitude, or other aspects, of tissue displacement. In another embodiment, element 56 comprises an ultrasound probe, such as a transcranial Doppler, that detects the Doppler shift produced by the tissue displacement. In yet another embodiment, detection element 56 comprises a hydrophone that detects the sound waves emitted by tissue in which an acoustic radiation force is generated.

Commercially available components may be used in systems of the present invention. The following description of specific components is exemplary, and the systems of the present invention are in no way limited to these components. High intensity focused ultrasound transducers are available from Sonic Concepts, Woodinville, Wash. Multi-element transducers have been used by researchers and are described in the literature. A multiple focused probe approach for high intensity focused ultrasound-based surgery is described, for example, in Chauhan S, et al., Ultrasonics 2001 January, 39(1):33–44. Multi-element transducers having a plurality of annular elements arranged, for example, co-axially, are suitable. Such systems may be constructed by commercial providers, such as Sonic Concepts, Woodinville, Wash., using technology that is commercially available. Amplifiers, such as the ENI Model A-150, are suitable and are commercially available. Diplexers, such as the Model REX-6 from Ritec, are suitable and are commercially available. Function generators, such as the Model 33120A from HP, are suitable and are commercially available. Many types of controllers are suitable and are commercially available. In one configuration, a Dell Dimension XPS PC incorporates a Gage model CS8500 A/D converter for data acquisition, and utilizes LabView software from National Standards for data acquisition and equipment control. In some embodiments, an ATL transcranial Doppler probe, Model D2TC, is used for detection.

In operation, the acoustic source/detector combination is stably mounted, or held, in proximity to a surface such that the foci of the acoustic sources are adjustable to provide an acoustic focal point within the target tissue. The acoustic source/detector combination is preferably provided as a unitary component, but separate components may be used as well. For analysis of CNS tissue, such as brain or optic nerve tissue for determination of ICP, for example, the acoustic source/detector combination may be mounted on a stabilizer, or in a structure, such as a helmet-type structure, that may be mounted on the head. Alternatively or additionally, an applicator containing an acoustically transmissive material, such as a gel, may be placed between the surface of the acoustic source/detector combination and the head. For localization of tissue responses, such as pain, to focal ultrasound probing, an acoustic source/probe combination may be provided in a holder that is steerable to facilitate probing of various targeted tissue sites within a general situs. Steering of the acoustic probe device may be accomplished manually or using automated mechanisms, such as electronic steering mechanisms. Such mechanisms are well known in the art.

Most tissue, including brain tissue, contains a variety of cell types and vasculature. To ensure that representative target tissue is sampled, the target tissue location must be volumetrically large enough to provide a representative sample. The volumetric sampling requirements will vary, of course, according to tissue type and location. In general, target sites having tissue volumes of from 1 mm$^3$ to about 100 cm$^3$ are suitable, and target tissue sites having tissue volumes of less than about 5 cm$^3$ are preferred. For assessment of ICP, vasculature and other conditions in the CNS, CNS tissue target sites having generally uniform vasculature and tissue type are preferred.

Data, such as acoustic scatter data, relating to intrinsic and/or induced tissue displacements is processed according to methods and systems of the present invention and related to medically relevant physiological properties, such as ICP, ABP, autoregulation status, and other disease states or tissue conditions. Exemplary data processing techniques for making various correlations based on various types of acquired data are described below. Although these data processing techniques are based on the acquisition of acoustic scatter data, they may be applied, as well, with modifications that would be well known in the art, in other modalities, such as near infrared spectroscopic (NIRS) modalities and magnetic resonance modalities.

ICP and Other CNS Tissue Properties Using Intrinsic Tissue Displacement ("Passive" Mode)

There are several alternative methods for relating clinical parameters, such as ICP, to intrinsic tissue displacements in a passive mode of operation. Several are described in detail below. These exemplary methods and techniques are provided for illustrative purposes only, and the methods and systems of the present invention are not limited to these examples.

Correlation of Non-Invasively Measured Spontaneous Tissue Displacement with ABP and ICP One method uses a derived relationship between spontaneous (intrinsic) tissue displacement (resulting from blood flow, CSF, etc.), determined by analyzing acoustic scatter from a CNS target tissue site, ABP, and invasively monitored ICP to estimate ICP from invasively or non-invasively measured tissue displacement and ABP. Using an ultrasound probe operating above 100 kHz, a given volume of tissue is insonated with a waveform having a specific frequency and amplitude, and the time or phase shift of a reflected ultrasound signal is used to calculate intrinsic tissue displacements. The equation that relates time or phase shift to tissue displacement is: d=t*1500 m/sec, where d=tissue displacement, t=the time or phase shift of the reflected signal, and 1500 m/sec is the estimated speed of sound through the brain. Since ICP=CPP−MAP, where MAP=(2*diastolic ABP+systolic ABP)/3, and d=F(CPP), where F can be any function, such as an exponential, vector, matrix, integral, etc., or a simply an empirical relationship with CPP, CPP=MAP−ICP=$F_2$(d), where $F_2$=$F^{-1}$. $F_2$ is determined empirically by taking measurements from a variety of patients under various circumstances, and the determination of displacement and ABP can then be used to calculate ICP, where ICP=$F_2$(d)−MAP.

Correlation of ICP with Amplitude of Acoustic Tissue Signal

This method uses a derived relationship between the amplitude of reflected acoustic signal(s) from CNS target tissue sites, ABP, and invasively monitored ICP to estimate ICP from non-invasively measured acoustic signals and ABP. Using an ultrasound probe operating above 100 kHz, a given volume of tissue is insonated with a waveform having a specific frequency and amplitude, and the amplitude of the backscatter is used to create a waveform of tissue reflection/absorption. This new waveform, α, can be generated by integrating the amplitude of the backscatter over a finite epoch (such as the cardiac cycle, measured with ECG tracing) and normalizing this by the time period of the epoch. Since the backscatter signal is related to the arterial pulse wave, α can be normalized to the MAP (as defined above), to produce a waveform β. The relationship between this normalized waveform, β, and invasively measured ICP is then determined by taking simultaneous measurements of the backscatter signal, ABP, and ICP and solving for the equation ICP=F(β), where F is any mathematical function, or simply an empirical relationship. Once F is established (by means of multiple empirical measurements from a variety of patients under various, known conditions), the non-invasive determination of β by the noninvasive determination of tissue displacement and noninvasive determination of arterial blood pressure can be used to calculate ICP.

Correlation Between Peak Backscatter Amplitude and ICP

In a manner similar to that described above, the peak amplitude of the backscatter signal over a given epoch (e.g., cardiac cycle) can be normalized by the MAP over the same epoch, producing a value, *, and this related with simultaneous invasive measurements of ICP to generate a relationship, ICP=F(*), where F is a mathematical or empirical relationship between * and ICP.

Many attempts have been made to infer ICP and/or autoregulation status using standard transcranial Doppler (TCD) data. In another embodiment, methods and systems of the present invention use existing assays of noninvasive ICP, based on standard TCD measurements, replacing non-invasive measurements of mean velocity in the middle cerebral artery with noninvasive measurements of the displacement of CNS tissue caused by blood flow, the cardiac cycle and respiration. One such example is provided below, based on the work of Schmidt, B., et al., *Noninvasive Prediction of Intracranial Pressure Curves Using Transcranial Doppler Ultrasonography and Blood Pressure Cures*, Stroke Vol. 28, No. 12, December 1997. The processing steps of the present invention require simultaneous and continuous measurements of invasive ICP, invasive or non-invasive ABP, and displacement (or the like) to generate a set of equations that accurately predict ICP using only noninvasively-determined displacement and ABP data alone, as follows:

Step 1: A weight function is calculated between ABP and ICP, using a system of linear equations. The solution of this system of equations results in a vector containing the coefficients of the weight function. Any number of coefficients can be chosen to model this system. For example, we will select 25 coefficients. For any given weight function ($f_0$, $f_1$, ..., $f_{24}$), the ICP value at point k in the time sequence can be computed by the values of the AP recorded at time k-24, k-23, ..., k-1, k according to the formula $ICP_k$=$f_0$*$ABP_k$+$f_1$*$ABP_{k-1}$+ ... +$f_{23}$*$ABP_{k-23}$+$f_{24}$*$ABP_{k-24}$.

Step 2: The coefficients of a weight function between displacement and ABP curves are used as movement characteristics. The computation is similar to the one described in Step 1 and performed at the same time. Again, any number of coefficients can be used; we will select 6 for this example.

Step 3: The relationships between the movement characteristics of Step 2 and the 25 coefficients of the weight function in Step 1 are described by an approximating linear function (i.e., matrix A and vector B), which is calculated through a sequence of 25 multiple regression analyses of the patients' data.

After Steps 1–3 are performed, the noninvasive ICP determination is made as follows: while the displacement (or the like) and ABP curves are recorded noninvasively for a new patient (one not used in the derivation of the above simulation function), the movement characteristics are computed every 10 seconds and transferred to the simulation function. Finally, the simulation function transforms the ABP curve into a simulated ICP curve.

Arterial Blood Pressure Using "Passive" or "Active" Mode

In another aspect of methods and systems of the present invention, intrinsic and/or induced changes in the diameter or other geometric properties of a blood vessel, or changes in the intrinsic or induced displacement in tissue surrounding blood vessels, are monitored and assessed using ultrasound, and this information is related to synchronous Doppler flow measurements within the same vessel. In an active mode, tissue displacement and associated emissions may be induced in a blood vessel or in tissue surrounding a blood vessel by application of an acoustic radiation force, as described above. Similarly, in a passive mode, intrinsic tissue displacements at or near a blood vessel may be detected using a variety of techniques, with the use of ultrasound techniques being preferred. In some embodiments, an initial assessment is performed, using Doppler flow measurements or ultrasound detection techniques, to locate a desired blood vessel and thereby provide a focus for identifying intrinsic and/or induced displacements at or near the vessel.

Since the diameter (or other geometric properties) of the vessel is a function of the pressure being exerted against the wall of the vessel by blood, and since the velocity of blood flow is dependent on the diameter (or radius) of the vessel through which the blood travels, blood pressure can be calculated from flow velocity measured by Doppler. Geometric properties of vessels that may be evaluated using methods and systems of the present invention include changes in diameter, cross-sectional area, aspect ratio, rate of change of diameter, velocity, and related parameters. By simultaneously measuring the pulsatility of the blood vessel of interest and the Doppler flow velocity proximal and distal to this site, continuous blood pressure is determined. Specific methods for assessing ABP are described below.

Blood pressure may also be assessed, in an active or passive mode, by examining acoustic properties of target tissue sites at or in proximity to blood vessels. The acoustic properties of target tissue at or in proximity to blood vessels can be related to tissue stiffness or compliance, which can be related to blood pressure, in much the same way that tissue stiffness in the CNS is related to ICP.

Blood pressure measurements made using the passive or active acoustic modes described herein may also be used for calibration of existing invasive or non-invasive blood pressure monitoring devices. Thus, the methodology described below, particularly with reference to blood pressure determinations using the active acoustic mode, may used in combination with existing blood pressure monitoring devices, which are available, for example, from Medwave Corporation, St. Paul, Minn.

Correlation of Non-invasively Measured Spontaneous Vessel Wall Displacement with Doppler Flow and ABP This method uses a derived relationship between spontaneous vessel wall displacement (due to blood pressure and smooth muscle tonal responses to the hemodynamic state), synchronous velocity of blood flow within the vessel of interest, and invasively monitored ABP to estimate ABP from non-invasively measured vessel wall displacement and Doppler flow velocity. Using an ultrasound probe, the given vessel of interest is insonated with a waveform of specific frequency and amplitude, and the time or phase shift of a particular reflected or backscattered or echo signal is used to calculate spontaneous tissue displacement.

The equation that relates time or phase shift to tissue displacement is $d=t*1500$ m/sec, where d=tissue displacement, t=the time or phase shift of the reflected signal, and 1500 m/sec is the estimated speed of sound through tissue. The relationship between d, synchronously measured Doppler flow velocity within the vessel of interest (i), and invasively measured ABP is then determined by taking simultaneous measurements of spontaneous vessel wall displacement, flow velocity, and ABP and solving for the equation: $ABP=F(d, i)$, where F can be any function, such as an exponential, vector, matrix, integral, etc., or a simply an empirical relationship. Once F is established (by means of multiple empirical measurements from a variety of patients under various circumstances), the non-invasive determination of vessel wall displacement and flow velocity is used to calculate ABP. A calibration step using, for example, a cuff plethysmograph to measure ABP, may be implemented before continuous, noninvasive ABP measurements are made.

Correlation of ABP with Amplitude of Vessel Wall Signal and Doppler Flow Velocity This method uses a derived relationship between the amplitude of the reflected vessel wall signal, Doppler flow velocity, and invasively monitored ABP to estimate ABP from non-invasively measured vessel wall signal and Doppler flow velocity (i). Using an ultrasound probe, a particular vessel of interest is insonated with a waveform of specific frequency and amplitude, and the amplitude of the backscatter is used to create a waveform of vessel wall reflection/absorption. This new waveform, $\alpha$, is generated by integrating the amplitude of the backscatter over a finite epoch (such as the cardiac cycle, measured with ECG tracing) and normalizing this by the time period of the epoch. The relationship between this derived waveform, $\alpha$, and invasively measured ABP is then determined by taking simultaneous measurements of the backscatter signal, Doppler flow velocity, and ABP and solving for the equation: $ICP=F(\alpha,i)$, where F can be any mathematical function, or simply an empirical relationship. Once F is established (by means of multiple empirical measurements from a variety of patients under various circumstances), the non-invasive determination of $\alpha$ can be used to calculate ABP. A calibration step using a cuff plethysmograph to measure ABP may be implemented before continuous, noninvasive ABP measurements are made.

Correlation Between Peak Backscatter Amplitude and ABP

In a manner similar to that described above, the peak amplitude of the backscatter signal over a given epoch (e.g., cardiac cycle) is normalized by the baseline value of the backscatter signal over the same epoch, and this, along with Doppler flow velocity, is related to the simultaneous invasive measurements of ABP. A calibration step using a cuff plethysmograph to measure ABP may be implemented before continuous, noninvasive ABP measurements can be made.

ICP and Other CNS Tissue Properties Using Induced Tissue Displacement ("Active") Mode In both the first and second active modes of operation, wherein induced tissue displacement is assessed, for example, an initial environmental assessment is generally performed to determine various parameters of the environment between the acoustic source(s) and the target tissue, so that that an appropriate acoustic force may be applied to the target tissue, such as the brain. Environmental factors, such as the distance between the acoustic transducer and various structural features, such as the brain surface, the thickness of the skull, the thickness of the dura, arachnoid, pial and CSF layers, impedance mismatches between the various structures and tissues, and the like, may be determined. The initial environmental assessment is determinative of various method and system parameters. Environmental assessments are preferably updated at intervals throughout a diagnostic or monitoring procedure.

The distances between various biological structures that an acoustic wave encounters as it propagates from the surface of the head to the brain, vary among individuals. The environmental analysis is therefore recommended, at the time of measurement, to supplement or refine epidemiological analyses done a priori. Short pulses of high frequency ultrasound may be used, for example, to identify the temporal distance from the acoustic source to the edges of biological structures having different properties, such as bone, fluid, dura matter, brain tissue, and the like. With knowledge of the sound speed in each type of biological structure and the temporal distance traveled by each pulse, the thickness of each section can be measured. The attenuation of the acoustic pulse that created the desired radiation pressure pulse is a function of the distance traveled through each sector and the attenuation coefficient of each material. Given values of attenuation from the literature or epidemiological studies for a multiple layered system, separate pulses may be directed to each layer to remotely determine the thickness of biological structures and the impedance mismatch between the structures.

In a "layer stripping" technique, one can administer a series of pulses to determine refined values of the impedance (density times sound speed) mismatch between adjacent tissues, provided information relating to the attenuation in the tissues of interest is available. Alternatively, the values for sound speed or density of the tissues of interest may be refined via this process. The stripping method is accomplished by first sending a pulse of sound, having a known amplitude and high frequency, from the transducer, through a well-characterized coupling medium, towards the skin or skin/fat/muscle complex, depending on the wavelength of the palpation pulse (the former if the palpation pulse is of relatively high frequency, the latter if it is of relatively low frequency). A measurable amount of sound reflects back to the acoustic receiver, whose amplitude is related, through well-established formulae and known values of attenuation and thus, through the product of the density and sound speed of the coupling medium, to the impedance of the skin or the skin/fat/muscle complex. A second acoustic pulse may then be administered, the second pulse having a wavelength optimized to generate a significant reflection from the next significant layer. The impedance of that layer may thus be characterized, as described above. This process may be repeated for the various intervening layers, until one determines the impedance of the brain, for example. Comparable stripping methods for other useful acoustic parameters may be similarly constructed, provided that good estimates are available for a different subset of the acoustic parameters necessary to characterize the amplitude of sound received at the brain surface, relative to that sent from the palpation transducer. Such empirical data relating, for example, distances between and attenuation coefficients of various biological structures, may be used and incorporated in a control system for predicting environmental parameters according to the present invention and, ultimately, for determining the amount of sound reaching the brain's surface to induce the deformation of that surface.

In an alternative embodiment, which would benefit from the environmental assessment just described, an acoustic pulse of a known amplitude ($A\_0$) may be administered at the frequency of the palpation signal towards the brain surface. There are multiple reflections of this pulse from the intervening tissue layers (skin or skin/fat/muscle, bone, dura, etc.), but the pulse directly reflected from the brain and first arriving at the acoustic receiver has the largest, if not the only, Doppler shift. This first Doppler-shifted pulse received by the diagnostic ultrasound device has an amplitude ($A\_1$)=$a^2 A_0 R$, reduced by a factor of "a" from the amplitude of the administered signal as a result of the propagation of the calibrated, diagnostic pulse through the intervening environment, both towards and away from the brain surface, and reduced because only part of the incident pulse is reflected back from the brain surface with a reflection coefficient R, which is a known function of the impedance mismatch between the brain and the adjacent layer, determined by the stripping method noted above. With this information, the amplitude ($A\_2$ defined as $aA_0$) of the sound received at the brain surface may be calculated in terms of known quantities as follows: $A\_2=(A_0 A_1)/R$. The amount of sound reaching the brain's surface to induce the deformation of that surface may thus be determined. Also, by detecting the Doppler-shifted signal, the location of the brain surface relative to the transducer may be determined.

After the environmental assessment, and in a first mode of operation, an acoustic radiation force is applied to a predetermined spatial location in a target tissue to produce deformation of the target tissue. One or more acoustic sources may be used. A single acoustic transducer may serve both as an acoustic source and detector. The one or more acoustic sources may have fixed, non-adjustable foci that correspond to a desired target tissue location. Alternatively, the one or more acoustic sources may have variable foci, individually and with respect to one another, so that the focus of one or more sources may be adjusted for different target tissue locations and subjects. For operation in the first mode, the acoustic source(s) are operated, in phase, to produce a radiation force, at their foci, that deforms the tissue. If $\Delta\omega$ is zero, or one acoustic source is inactivated, the result is a unidirectional displacement of the brain with a negligible oscillatory component, at the PRF of the device. For operation in both modes, the acoustic sources may be phase and/or frequency modulated to produce oscillation of the tissue at a desired target tissue location.

During application of the radiation force and deformation, or shortly following application of the radiation force, another diagnostic probe pulse may be used to quantify an aspect of the deformation and, hence, provide information concerning tissue properties and/or ICP. A diagnostic ultrasound probe may be operated, for example, in any of the standard A or B or M modes. For example, the diagnostic ultrasound probe may be used to image the displacement when run in standard B-mode imaging, or to follow the displacement as the movement in time of the return of the diagnostic pulse reflected from the brain surface. The schematic diagrams of FIGS. 5A–5C illustrate: (1) the undisplaced brain surface prior to application of the radiation force producing deformation (FIG. 5A); (2) the displaced brain surface resulting from application of the radiation force, having a maximum amplitude Z (FIG. 5B); and (3) the relaxation of the brain tissue to the undisplaced condition following inactivation of the acoustic source(s) (FIG. 5C). The transiently induced displacement, illustrated at FIG. 5B, will emit sound as it eventually relaxes to its pre-deformed state (FIG. 5C). A suitable diagnostic ultrasound probe operated as a hydrophone may receive the emitted acoustic signal, which may be used alone or in combination with displacement data, to assess the physiological state or condition of the tissue.

The schematic diagrams of FIGS. 5D–F illustrate the acoustic wave reflected from the surface of the brain as a function of time, as well as the simplest and most empirical embodiment of the proposed noninvasive means of quantifying ICP. In the undisplaced tissue surface condition when no radiation force is applied, shown in FIG. 5D, the reflected acoustic wave is detected at time t. When a radiation force is applied to induce tissue deformation, detection of the reflected acoustic wave is delayed by a time $\Delta t$, as shown in FIG. 5E. The tissue then relaxes to its original, undisplaced condition, and the reflected acoustic wave is again detected at the original time, t, as shown in FIG. 5F. If desired, knowing the sound speed in CSF, one can translate this into a spatial displacement Z. One may relate either of $\Delta t$ or Z, in a purely empirical manner, to the intracranial pressure.

As an example of how to use this information to noninvasively determine ICP in a way related more directly to first principles, consider the formula of Sadowsky (1928) Z Angew Math Mech 8, 107 quoted in Sarvazyan et al (1995) Biophysical bases of elasticity imaging, in: Acoustical Imaging V21, edited by Sarvazyan for Plenum Press, NYC:

$$F=8*G*R*Z(1+(G/K)/(1+(G/3K)))^{\wedge}(-1)$$

where F is the force exerted uniformly over a portion of the surface with radius R of a viscoelastic solid with shear modulus G, and compressional modulus K that produces a deformation of the viscoelastic solid whose maximal extent is Z. For such a material, $G*2*(1+v)=E$ where "v" is Poisson's ratio and E is Young's modulus. Note that for most biological materials, G/K is quite small, so that this formula reduces, in practice, to: $F=8*G*R*Z$.

The equation quoted earlier by Chu and Apfel is used to calculate the net force exerted on the brain by focused ultrasound with a circular cross-section with radius R and area $PI*R^2$, which, in turn, can be placed in the formula for F to produce a formula for G, the shear modulus of the brain:

$$G=2(rho\_1/rho\_0)*K*<E>*(1+(rho\_1*c\_1)/(rho\_0*c\_0)^{\wedge}(-2)*(PI*R)/(8*Z)$$

G gives a measure of the ability of the brain to support shear stress. As noted above, it is intimately related to the ability of the brain to support compressional stress. As such, its value in brain should be directly, perhaps linearly, related to the ICP of the brain. One can therefore estimate ICP by evaluating the formula noted above and, through empirical means, relate G to ICP.

One method for performing the empirical step is described below. One may determine, as a function of patient population (likely age and race), the average density of the brain (medium 1) and CSF or bone (medium 2), and the nonlinearity parameter K. The ratio of the impedances of medium 1 and 2 may be refined, if not actually determined, using the "layer stripping" technique described above. The energy density of the incident acoustic beam may be may be calculated as described above by measuring the amplitude of the acoustic pulse at the brain surface. Finally, the acoustic beam may be designed to have a circular cross-section with radius R. The acoustic beam will have at least a weak gradient in acoustic intensity. The nonuniformity of the acoustic beam is therefore taken into account by defining an "effective" radius of the acoustic beam, i.e., a radius over which a significant majority of the radiation pressure is generated. Also of concern is the possibility of scattering or deformation of the shape of the acoustic beam by irregularities in the bone surface on the scale of R. These effects may be minimized by applying the ultrasound to well-known places on the skull where horizontal gradients in bone properties (thickness, attenuation, density, sound speed, etc) are known.

It is possible to estimate the deflection of the brain surface using values of the parameters in the literature and the following form of the equation:

$$\frac{\Pi}{4} R \frac{e_0}{e_1} \frac{k}{G} \frac{<Ii>}{C_0} \left(1 + \frac{e_1 c_1}{e_0 c_0}\right)^{-2} = z$$

Where $\rho_i$ is about 1 kg/m$^3$, G is about $10^3$–$10^4$Pa, $C_i$ is about $1.5 \times 10^3$ m/s, K is about S, and $<E_i> = <I_i>/C_0$ where $<I_i>$ is the time average spatial peak intensity of the sound incident on the brain surface. This equation reduces down to the following solution: Z is between $R<I_i> \times 10^{-7}$ m and $R<I_i> \times 10^{-6}$ m.

Based on published work, $<I_i>$ is less than $10^2$–$10^3$ w/cm$^2$, or $<I_i>$ is less than $10^6$–$10^7$ w/m$^2$, in the units necessary to evaluate the above formula. Also, based on existing devices that can easily achieve these intensities, R is between $10^{-3}$ m and $10^{-2}$ m. Therefore, Z is expected to range from about 100 micrometers to about 1 millimeter for R=$10^{-3}$ m, and from 1 millimeter to 1 centimeter for R=$10^{-2}$ m. These values may be smaller or larger, depending most directly on the intensity of the ultrasound at the brain surface. For example, Nightengale et al., *On the feasibility of remote palpation using acoustic radiation force*, J. Acoust. Soc. Am. 110(1), July 2001, use $I_i$ between 1–100 w/cm$_2$ with an R of about 5 mm and observe displacements Z ranging from 1–100 $\mu$m for tissues and phantom tissues satisfying the criteria above.

If the deflection Z of the brain is too small to measure directly, the Doppler shift associated with the deflection may be measured and related, that either empirically or via first principles, to the size of the deflection.

Note also that this embodiment of the proposed invention could in principle be used to at least calculate changes in ICP, or in the time course of ICP, if one can relax the requirement for a calibrated acoustic source. These changes in ICP, or in the time course of ICP, may be related to medical compliance.

In another embodiment, multiple displacements or emissions on variable time scales that are short with respect to the natural relaxation time of the tissue may be produced using a rapid succession of ultrasound pulses. In this embodiment, application of a first pulse of acoustic radiation force produces a well-defined tissue deformation or emission and, at a predetermined time during the displacement, a second acoustic force is applied, producing a displacement of the displacement and, in some cases, an associated emission. This embodiment is useful when the ratio of the amplitudes of the first and second displacements, or the ratio of the frequencies associated with the emissions, with the same radiation pressure, do not equal one. This may occur, for example, if the initial displacement changes the local blood supply (which, if useful, can be accessed by changes in diagnostic acoustic backscatter) and/or changes the blood-flow velocity (which, if useful, could be assessed by traditional TCD techniques). The amount by which a given pair of displacements or emissions differ from one another, or can change the local blood supply or velocity should be related at least to the local medical compliance of the brain (i.e. its capacity to absorb additional changes in intracranial fluid volume without excessive values of ICP), as well as to ICP. An advantage of this technique is that calibration of the environment is not necessary. That is, using this technique, we do not need to know the applied radiation pressure. Instead, what is necessary is that the user can generate a series of identical ultrasonic pulses that cause medically acceptable and measurable displacements of the brain tissue, and that the relationship described above is robustly applicable across well-defined members of the population.

In yet another embodiment that does not require knowledge of the amount of radiation pressure applied to the brain, but produces medically acceptable displacement(s) or emission(s) of the brain with usefully measurable properties, one can evaluate the ratio of the deformation or emission amplitudes, velocities, etc at the low and high points of the cardiac cycle, for example. Because of differences in perfusion and/or blood-flow rate, this ratio will not equal one and, as above, allows the assay of the time course of local medical compliance of the brain and of ICP using empirical means. It may be useful for this embodiment to be supplemented with ancillary measurements of the mean and variance of blood pressure.

In yet another embodiment that does not require a calibrated acoustic pulse, an acoustic pulse sufficient to produce a medically acceptable displacement of or acoustic emission from CNS tissue with usefully measurable properties is administered. The rate of relaxation of the displaced tissue (in particular, relaxation from its maximum extent, or the slope of the displacement, or any other geometric property of the displacement) and/or its associated acoustic emission (s) may be directly related to ICP: the higher the ICP, the higher the frequency of acoustic emissions and/or the stiffer the tissue and the more rapidly it will conform to its original geometric structure. Any of the higher rates of recovery from displacement or decay of the acoustic emission, or any of the rates of recovery from transient biological effects induced by the ultrasonic displacement may be used with methods of the present invention. These rates should be independent of the absolute value of the radiation pressure that produces the displacement, provided that the tissue remains in the "linear" viscoelastic regime. Tissue that is not permanently deformed by the ultrasound will remain in the linear viscoelastic regime.

In yet another embodiment that does not require a calibrated acoustic pulse, an acoustic pulse sufficient to produce a medically acceptable displacement of CNS tissue, such as the brain surface, is applied as a noninvasively applied acoustic radiation pressure, rather than a direct, manually applied pressure, as disclosed by Madsen et al (U.S. Pat. No. 5,919,144). Analytical techniques disclosed by Madsen et al. may be used to determine tissue stiffness and ICP and other related clinical parameters.

Methods of the present invention involving the "active mode" of tissue displacement may thus involve: (1) optionally, characterization of the acoustic propagation environment by conducting an initial environmental assessment to determine the location and properties of tissue between the source(s) and desired target tissue; (2) application of a generally known acoustic radiation force to displace the target tissue at a desired target location; (3) examination of at least one aspect of the displacement of the target tissue, or an induced biological response to the displacement of the target tissue induced by the radiation force; and (4) assessing a tissue property, including ICP, ABP, or other tissue properties described herein, as a function of an aspect of displacement of the target tissue or a biological response to the displacement of the target tissue.

Vibrating objects in contact with or in proximity to acoustically compressible tissue, such as the brain with the CSF, emit sound into the acoustically compressible tissue with the frequency of the vibration, and with an amplitude proportional to the amplitude of the vibration. According to a second active mode of operation, methods of the present invention may involve: (1) characterization of the acoustic propagation environment by conducting an initial environmental assessment to determine the location and properties of tissue between the source(s) and desired target tissue; (2) applying known acoustic radiation forces using one or more acoustic sources to oscillate the target tissue at a desired target location; (3) examining at least one aspect of the acoustic emission from the vibrated target tissue, or fluids in proximity to the target tissue; and (4) determining a tissue property, including ICP, ABP, and other properties described herein, as a function of at least one property of the acoustic emission. For example, the frequency and/or phase of multiple acoustic sources may be modulated to produce the desired maximum oscillation of target tissue, which itself can be determined as the PRF or frequency of the palpation is scanned through a range of values. Alternatively, one or a few palpations may induce emissions that can be monitored. A diagnostic probe may be used, in this embodiment, to detect the acoustic emission from the vibrated tissue. The amplitude of the acoustic emission is related to the tissue stiffness, or the Young's modulus, or shear modulus, of the target tissue, which is empirically related to the ICP.

In general, smaller amplitude displacements per unit acoustic radiation force, and smaller Doppler effects, indicate stiffer, less compliant tissue and, where ICP is determined, a higher ICP. Relatively greater amplitude deformations per unit acoustic radiation force, and higher Doppler effects, indicate softer, more compliant tissue and, where ICP is determined, a lower ICP. ICP and tissue properties determined using methods and systems of the present invention may be compared to empirical standards relating, for example, to skull thickness, various tissue properties and conditions, subject age, condition and other characteristics, and the like.

Tissue stiffness, particularly brain tissue stiffness, and its surface location and conformation, change with both the cardiac and respiratory cycles. If acoustic forces producing deformation or oscillation are applied quickly relative to these cycles, the time course of tissue properties or ICP may be measured, which may be of medical interest and significance, or may contain information relating to the magnitude of ICP. Patient motion may also produce movement of the probes, which would require an updated environmental assessment. According to one embodiment, the system and environmental parameters are updated rapidly relative to patient movement to reduce the effects of patient movement.

Autoregulation—Passive and/or Active Mode

A patient's autoregulation status, or autoregulation capacity, may also be determined using acoustic data related to intrinsic and/or induced tissue displacements according to the present invention, as described in greater detail below. ICP and autoregulation status, or autoregulation capacity, are intimately related. The net volume of blood within the brain at any time point within the cardiac cycle is a function of systemic blood pressure and protective autoregulatory mechanisms of the brain vasculature, from its major arteries, having diameters on the order of millimeters, to its arterioles, having diameters on the order of microns. These various physical scales of cerebral vasculature respond with different time scales and different levels of contribution to the determination of ICP and autoregulation. The different classes of cerebral vasculature have different material properties, such as Young's modulus, which contribute to the different displacement properties in the brain.

The brain receives a substantially constant rate of blood flow, which is determined by cerebral perfusion pressure (CPP), where CPP=MAP–ICP over a wide range of mean arterial pressures. In this way, under normal conditions, the brain and its vasculature are capable of altering CPP in order to maintain proper blood flow to the brain. This is referred to as a normal state of autoregulation. When the ability to alter CPP to maintain proper blood flow to the brain is lost, autoregulation is abnormal and ICP becomes directly proportional to the mean arterial blood pressure.

In one embodiment, using continuously acquired noninvasive CNS target site acoustic data relating to intrinsic and/or induced tissue displacement or emission, along with simultaneous noninvasive or invasive measurements of continuous ABP and transcranial Doppler flow velocity, the status of cerebral autoregulation is assessed. CPP is determined from the displacement or emission data and ABP data. Specifically, correlation coefficient indices between time averaged mean flow velocity (FVm) and CPP (Mx), and between the flow velocity during systole and CPP (Sx), are calculated during several minute epochs and averaged for each investigation. These correlation indices are determined for a variety of clinical situations in which autoregulation and outcome is known. From this, regression lines are determined to infer the status of cerebral autoregulation for any set of Mx and Sx values. See, Czosnyka et al, *Monitoring of Cerebral Autoregulation in Head-Injured Patients*, Stroke Vol. 27, No. 10, October, 1996).

In another embodiment, continuously acquired noninvasive acoustic data relating to tissue displacement(s) and/or emission(s) is used along with simultaneous measurements of continuous ABP, to determine the status of cerebral autoregulation. Specifically, a pressure reactivity index (PRx) is calculated as a moving correlation coefficient between a finite number of consecutive samples of values for displacement and/or emission and ABP averaged over several minutes. Thus, a continuous index of cerebrovascular reactivity (autoregulation) to changes in ABP is determined. A positive PRx is indicative of impaired autoregulation and predicts unfavorable outcome, while a negative PRx indicates intact autoregulation and likely good outcome. See, Czosnyka et al., *Continuous Monitoring of Cerebrovascular Pressure-Reactivity in Head Injury*, Acta Neurochir [Suppl] 71:74–77, 1998).

In another embodiment, spectral analysis of simultaneously acquired continuous, noninvasive acoustic data relating to tissue displacement(s) and/or emission(s) and continuous invasive or noninvasive ABP data is used to determine the status of cerebrovascular autoregulation. Transfer functions (TFn) are calculated from fast Fourier transform (FFT) spectra as ratios of displacement and/or emission and ABP harmonic peak amplitudes to distinguish states of vasoreactivity. TF are calculated for a variety of known clinical conditions, and this data is used to determine values for the TF that correspond to specific states of autoregulation. These TF values can differentiate impaired autoregulation from effects solely related to elevated ICP or active vasodilation. See, Nichols, J et al., *Detection of Impaired Cerebral Autoregulation Using Spectral Analysis of Intracranial Pressure Waves*, J. Neurotrauma vol. 13, No. 8, 1996.

Simultaneous acquisition of acoustic data relating to continuous tissue displacement and/or emission and invasive or noninvasive continuous ABP can also be used to calculate a correlation coefficient that serves as a gauge of cerebral vascular dilation. Displacement and/or acoustic emission (D) and ABP are simultaneously acquired at a rate of 250 Hz. The normalized correlation function of the two signals is computed as:

$$r(t) = E[D(t), ABP(t)]/\sqrt{E[D(t), D(t)] * E[ABP(t), ABP(t)]}.$$

The value of this function at the origin is the correlation coefficient for the two functions: it is an analytical measure of the similarity between the two signals which varies between −1 and 1. If the two signals are proportional, then the signals are strongly related, and the value is close to either −1 or 1, indicating that autoregulation is impaired; if the correlation coefficient is between −0.70 and 0.70, then the signals are not similar and autoregulation is likely intact. See, Daley et al., *Correlation coefficient between Intracranial and Arterial Pressures: A Gauge of Cerebral Vascular Dilation*, Acta Neurochir [Suppl] 71: 285–288, 1998).

To accurately determine ICP and/or the state of autoregulation, the hemodynamic and/or cerebrospinal systems may need to be perturbed for a finite period of time to cause a known alteration in ICP, or to challenge autoregulation. Several exemplary types of perturbations, involving physiological challenges, are described below:

1) Mechanical perturbations of the hemodynamic system for evaluation of autoregulation may involve the placement of large pneumatic or hydraulic blood pressure cuffs around the lower extremities and inflated in order to increase venous return to the heart, thereby increasing vascular blood volume, leading to increased blood flow to the brain. The state of autoregulation can be assessed by analysis of the Doppler information. Other means of increasing blood flow to the brain including placing the patient in a gravity suit, changing ventilatory parameters on mechanical ventilators for intubated patients, and restricting arterial blood flow to the periphery.

2) Pharmacological perturbations of hemodynamic system for evaluation of autoregulation. If autoregulation is intact, the brain can respond to this decreased blood flow by re-directing blood flow and altering resistance to ensure that it receives adequate perfusion. Alternatively, intravenous fluid boluses can be administered to transiently increase blood volume and flow to the brain. If autoregulation is intact, the brain can respond accordingly. Other means for altering the blood volume and flow include the use of vasopressors, vasodilators, chronotropic and contractility agents.

3) Changes in patient position that alter ICP (e.g., Trendelenberg vs. reverse-Trendelenberg position) and changes in patient equilibrium, such as coughing, sneezing, etc., that alter ICP.

4) Modulation of mechanical ventilator input and output that alters intrathoracic pressure.

Under most circumstances, patients with intact autoregulation and normal ICP can tolerate any change in head body position, including head down or head up positions. Even in the fully normal, healthy individual, there is a transient change in ICP that is associated with such alterations in body position; within a few seconds, however, the body compensates and ICP returns to normal. It is conceivable that a change in body position, for example, will be required to cause a known change in ICP or autoregulation in order to calibrate or re-set the method used to noninvasively determine ICP and autoregulation.

Although specific applications for systems and methods of the present invention have been described in detail with reference to the non-invasive assessment and monitoring of intracranial pressure (ICP), similar methods and systems may be used, as well, for diagnosis and monitoring of diseases and conditions that are characterized by physical changes in tissue properties, such as Alzheimer's disease, multiple sclerosis, ischemic conditions, hyopoxic conditions, subdural and epidural hematomas, subarachnoid hemorrhage, intracerebral hemorrhage, tumors and other extra-cranial masses, and the like. Additional process steps may include assessment of tissue properties at multiple predetermined locations within target tissue, and comparison of tissue properties at different locations with empirically determined data, or with comparative tissue property data from other tissue types or locations.

Methods and systems of the present invention may be used in a variety of settings, including emergency medicine settings such as ambulances, emergency rooms, intensive care units, and the like, surgical settings, in-patient and out-patient care settings, residences, airplanes, trains, ships, public places, and the like. The techniques used are non-invasive and do not irreversibly damage the target tissue. They may thus be used as frequently as required without producing undesired side effects. The methods and systems of the present invention do not require patient participation, and patients that are incapacitated may also take advantage of these systems. The methods and systems for assessing tissue properties, including ICP, may be used on a continuous or intermittent basis for monitoring tissue properties or ICP.

All of the publications described herein, including patents and non-patent publications, are hereby incorporated herein by reference in their entireties.

The following examples are offered by way of illustration and are not intended to limit the invention in any fashion. The data supporting Examples 1 and 2 was collected using a specific embodiment of the apparatus of FIG. 2 without transducer 13 and its supporting electronics duplexer 15, amplifier 17 and function generator 19.

EXAMPLE 1

Figure 6A:
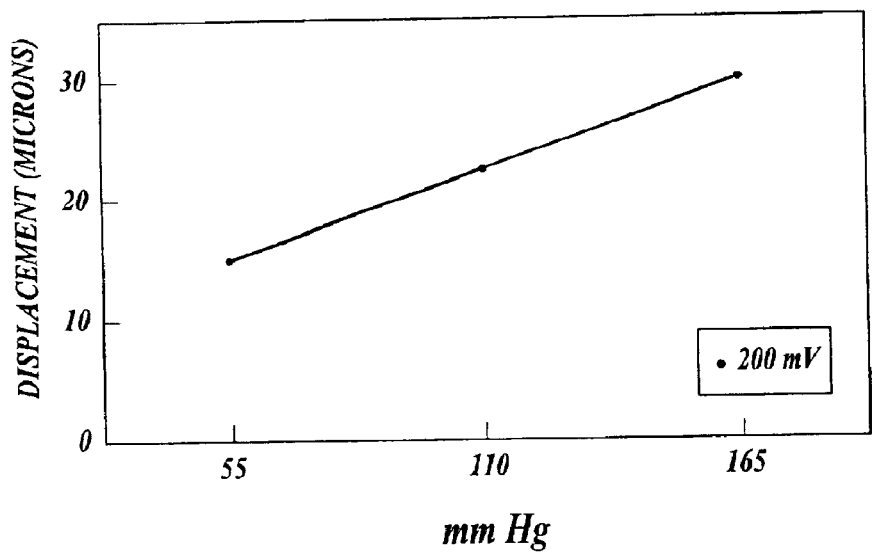
FIG. 6A shows a plot demonstrating measured displacement of in vitro beef brain as a function of increasing simulated ICP and as a consequence to increasing brain CSF volume.

We have shown in vitro (FIG. 6A) and in vivo (FIGS. 6B–D) and describe in detail below, that intrinsic displacements of brain tissue (e.g. compressions and distensions), and their various acoustic scatter properties, can be directly measured using a standard transcranial Doppler (TCD) transducer, off-the-shelf data acquisition systems, and novel analysis of the acoustic backscatter signal from brain.

An in vitro model for examining changes in ICP using acoustic techniques was constructed using fresh bovine brain immersed in fluid in a water-tight, visually and acoustically transparent bottle attached to a hand-pump for changing the pressure on the brain. An acoustic transducer (ATL/Philips Medical Systems, Bothell, Wash.), and the bottle, were placed in water so that the focus of the interrogation transducer was near the edge of the brain, but within the brain. Using a transducer whose amplifier was driven at 200 mV and a LeCroy Waverunner oscilliscope, we collected acoustic waveforms backscattered from the brain generated by the interrogator that showed, measured by changes in arrival times, that increases in displacement of beef brain as a function of increased pressure on the in vitro beef brain, as determined by a gauge on the hand pump, were linearly related (See FIG. 6A). This was the expected result: as the pressure on the brain (ICP) increases as a consequence of increasing liquid (CSF) volume in a confined space, we would expect to see the brain move away from the container.

Figure 6B:
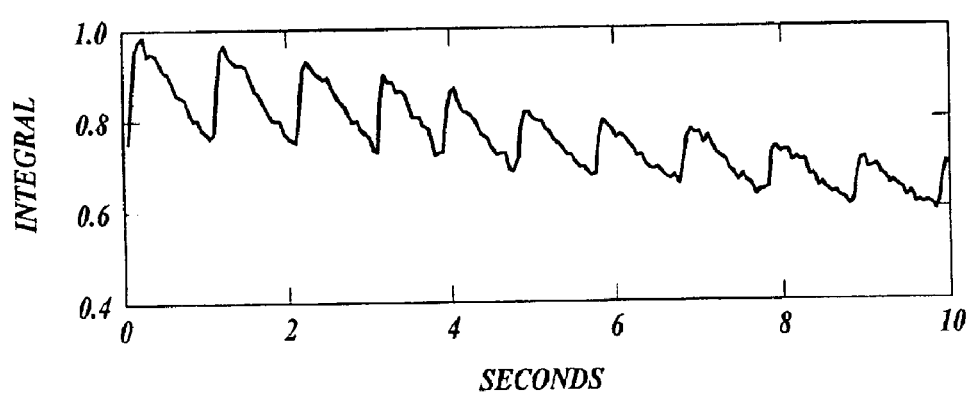
FIG. 6B shows a backscatter trace of human brain, in vivo, while the subject was holding his breath.
Figure 6C:
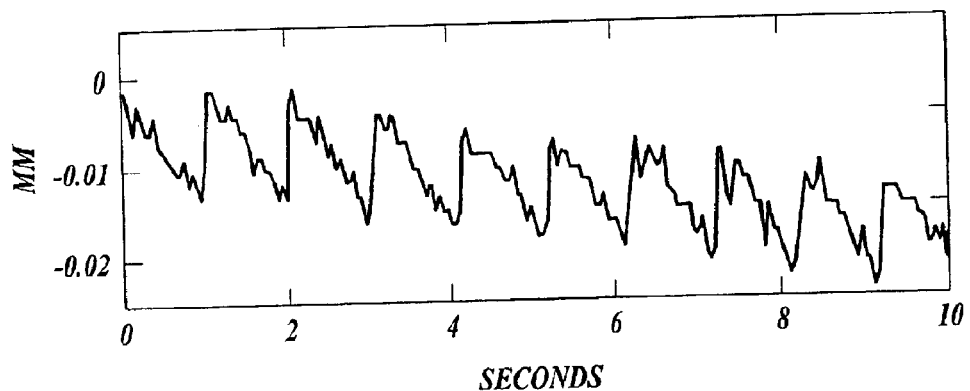
FIG. 6C shows the displacement of human brain, in vivo, while the subject was holding his breath.
Figure 6D:
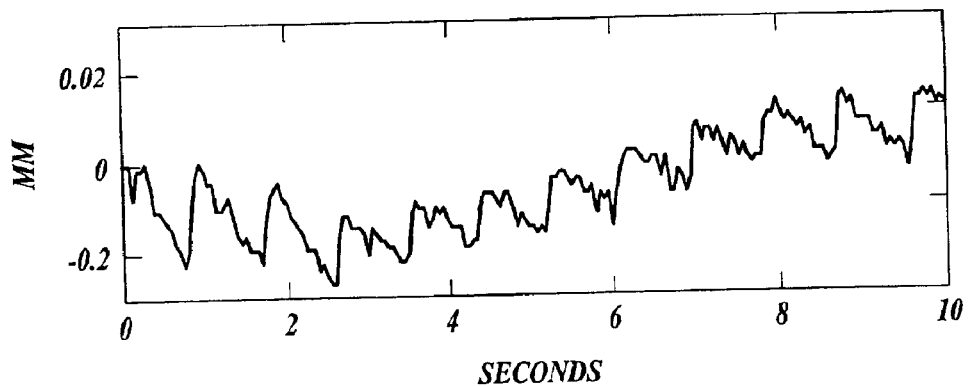
FIG. 6D shows the displacement of human brain, in vivo, while the subject first held his breath and then inhaled.

The displacement (compression and distension) waveforms shown in FIGS. 6B–D were produced using ultrasound techniques to measure acoustic scatter signals associated with intrinsic displacements of human brain tissue in situ. An acoustic transducer (ATL/Philips Medical System, Bothell, Wash.) was used to insonate target CNS tissue with acoustic interrogation signals having $10$–$10^3$ acoustic pulses per second at 2.25 MHz containing 3–15 cycles of ultrasound with peak negative pressures less than 2 MPa or 20 bar. Using a LeCroy Waverunner oscilliscope, we collected acoustic waveforms backscattered from the brain generated by the interrogator and calculated the tissue displacement.

This calculation was made using a normalized correlation of paired received signals. Given an estimate of the speed of sound in brain and the calculated temporal displacement, the spatial displacement of the tissue at a given moment may be calculated. Tracking the spatial displacement over time provides a direct measure of the displacement of the brain tissue that is being noninvasively interrogated by the diagnostic ultrasound. This calculation can also be made by correlating the backscattered signal with a reference interrogation signal, noting when the interrogation signal is sent and when the backscattered signal is received. Changes in the amplitude of the backscatter from the region of interest may also be monitored to determine the ICP waveform. For example, we have found that by integrating the acoustic backscatter signal over a short time interval of about 5 to 10 ms at the region of interest, and normalizing that integral by the length of that time interval, we developed a time series that has the salient features of the signal of FIG. 1A. In particular, for small volumes of measured brain displacement, the signal derived from following displacements or from following the normalized integral of the backscatter looks identical to the time course of the mean velocity of blood in the middle cerebral artery of the test subject.

FIGS. 6B–D show changes in properties of a human brain over time, measured in situ, using ultrasound techniques according to the present invention, as described above. Certain physiological behaviors, such as holding breath, sneezing, etc., are known to transiently increase or decrease ICP.

Figure 1B:
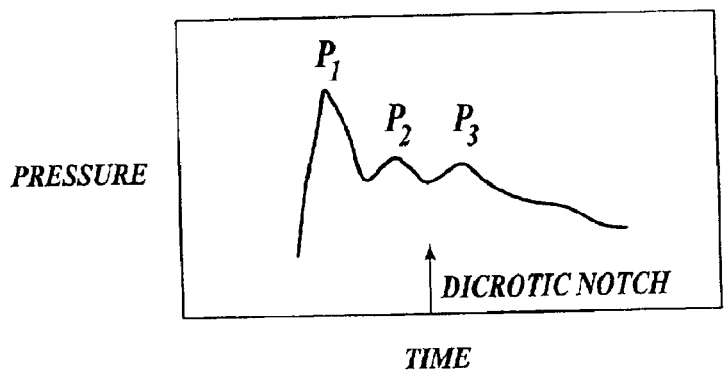
FIG. 1B shows an enlarged view of the ICP waveform enclosed by the box in FIG. 1A.

FIG. 6B shows changes in the normalized amplitude of the acoustic backscatter as the human subject held his breath. FIG. 6C shows the displacement of human brain as the human, based on correlation techniques, while the subject was holding his breath, using pulses with 15 cycles of ultrasound. In particular, FIG. 6C shows the net increased displacement of brain towards the transducer as the pressure on the brain increased due to an accumulation of blood volume in the brain, along with the cardiac-induced brain displacement signals similar to those seen in FIG. 1B.

FIG. 6B shows the same kind of received signal characteristics as FIG. 6C, where we used pulses with 5 cycles, but analyzed the data by integrating over the acoustic backscatter signal as described above. As in FIG. 6C, both waveforms changed over the 10 seconds while the subject held his breath, consistent with known transient changes in ICP when subjects hold their breath. The vascular pulse and autoregulation waveforms are present, in modified form, in FIG. 6C, as they are in FIG. 1B. The time series of FIGS. 6B and 6C look similar to the velocity pattern found in the patient's middle cerebral artery (data not shown). This measurement is therefore an accurate representation of the compression and distension of brain parenchyma in response to the major cerebral arteries, supplemented by contributions from the rest of the cerebral vasculature.

FIG. 6D shows an example of changes in near-surface brain displacement as the subject first held his breath for 2–3 seconds, then inhaled. Changes in respiration and the respiratory cycle are known to transiently change ICP. At first, the brain surface's net displacement toward the transducer increased. Upon inhalation, the brain tissue moved, over several cardiac cycles, away from the transducer. The observed displacement is consistent with the transient changes in ICP expected when a subject holds his breath (transient blood volume and ICP increase) and then inhales (transient blood volume and ICP decrease).

Our measurements were made over a small volume of brain tissue (of order 1.0 $cm^3$). We anticipate that measurements of brain tissue displacement (e.g. compression and distension) of a relatively large volume of brain tissue (on the of order 10 $cm^3$) will produce a signal that looks identical to the ICP trace of FIG. 1A. This signal is used directly, or with ABP data, to assess ICP and/or autoregulation status, as discussed above. Contributions to the acoustic backscatter signal over a large volume of brain tissue are the result of the average displacements (distension and compression) of brain tissue produced by a plurality of cerebral blood vessels, whose particular intrinsic oscillations will cancel, except for the major ones (dicrotic notch, etc), which will reinforce one another, as observed invasively.

EXAMPLE 2

We have shown, in vitro, using a beef brain model similar to that described above, that a palpation pulse of ultrasound across a range of acoustic intensities can cause increasing displacements of brain without causing gross tissue damage.

Fresh bovine brain was immersed in fluid in a water-tight, visually and acoustically transparent bottle attached to a hand-pump for changing the pressure on the brain. ATL acoustic transducers (ATL-Philips Medical Systems, Bothell, Wash.), and the bottle, were placed in water so that the focus of the acoustic palpation and interrogation transducers were near the edge of the brain, but within the brain. Using LeCroy Waverunner oscilloscope, we collected acoustic interrogation waveforms backscattered from brain. For palpating and interrogating beef brain, in vitro, the interrogation pulses were administered as described with respect to FIG. 6A, while the palpation pulses had a pulse repetition frequency of 1 Hz, contained 30,000–50,000 cycles, and had a time-averaged intensity of less than 500 W/$cm^2$.

Figure 7:
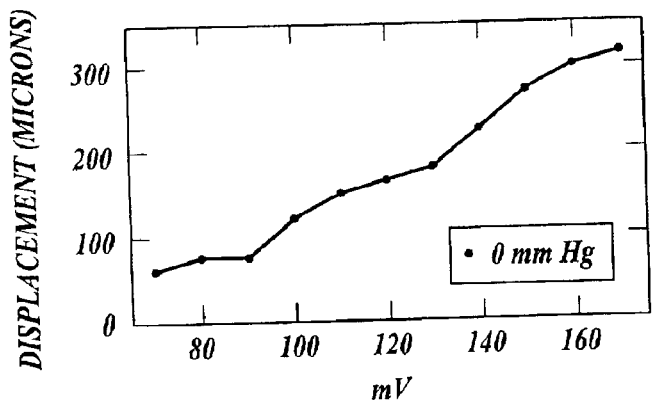
FIG. 7 illustrates experimental results showing that the measured displacement of brain tissue, in vivo, is proportional to the acoustic radiation force applied, as indicated by the acoustic driving voltage.

As shown in FIG. 7, as the acoustic force of the ultrasound increases (proportional to the driving voltage given in mV) at ambient (0 mmHg) pressure, so does the measured displacement of the beef brain, given in microns. We have also shown in the experimental beef brain model described above, in vitro, that brain displacement due to identical ultrasonic palpation pulses decreases from 300 μm to 210 μm as the pressure on the brain increases from 0 to 55 mmHg. Therefore, when the same acoustic force is applied with ultrasound, brain-tissue displacement in vitro is inversely proportional to ICP, as expected. Noninvasive, ultrasound-based measurements of ultrasonic palpation of brain tissue can be safely used to directly measure ICP in humans, without the need for blood pressure measurements, because by this method the brain will be subjected to a known (ultrasonic) force. Alternatively, using a focused ultrasound beam with an intensity less than a value easily determined to be safe, probing or palpation of brain tissue with a known force will also yield data ancillary to the passive method of ICP determination, by calibrating the amount of deformation brain tissue undergoes when subjected to a known compressive force.

EXAMPLE 3

Existing transcranial Doppler (TCD) devices and controllers may be modified to process raw data relating to tissue displacement according to methods and systems of the present invention. As data, such as Doppler information, is acquired by an ultrasound transducer/receiver, it is conventionally passed through a set of filters designed to eliminate portions of the signal attributable to the motion of the vessel wall, tissue displacement, CSF perturbation etc., leaving only the portion of the signal attributable to blood flow for subsequent transcranial Doppler analysis. For the present application, the unfiltered signal acquired by a TCD device, including portions of the signal attributable to blood vessel wall motion, brain tissue displacement and CSF pertubation, as well as blood flow, may be used according to methods of the present invention to assess CSF tissue properties, such as ICP.

Unfiltered data acquired by an ultrasound transducer/receiver in a TCD or a similar device may be processed alone, or in combination with data relating to arterial blood pressure, according to methods described above to assess ICP, autoregulation status, or the like. The analysis may include correlating the Doppler information with ABP information, performing Fourier analysis of the Doppler and ABP waveforms, and combining the Doppler and ABP information, as described above, to determine ICP and the state of autoregulation.

To construct a noninvasive ICP monitor using methods and systems of the present invention and existing technology, a continuous ABP monitor is used. Suitable ABP monitors that operate noninvasively are available, for example, from Medwave Corporation, St. Paul, Minn., under the tradename Vasotrac. Invasive ABP monitoring systems, such as are available from SpaceLabs Medical, Inc., Redmond, Wash., USA. These systems, or similar systems, are modified to provide arterial blood pressure information to another processor that analyzes the ABP data, along with TCD data, to yield ICP (as above).

Alternatively, a noninvasive ICP monitor using methods and systems of the present invention and existing technology may be constructed by modifying a TCD device to provide processing of raw Doppler data and correlation with ABP to yield ICP (as above). Suitable commercial TCD devices are available, for example, from Spencer Technologies, Seattle, Wash. under the tradename TCD100M.

Alternatively, an integrated unit that combines the above two components and a processor may be assembled using available commercial components, thus providing simultaneous displays of ABP, ICP, and autoregulation. FIG. 8 illustrates sample device output display for monitoring ICP, ABP and autoregulation status. The ICP output is expressed in mmHg over time, ABP output is expressed as mmHg over time, and may include a breakdown of systolic, diastolic and mean blood pressure, and autoregulation is expressed as a correlation factor R that is proportional to ICP and ABP over time. For each of the parameters, a status (normal, abnormal, etc.) display may be provided, and an alarm may be provided and set to be activated when a parameter exceeds or falls below predetermined threshold values.

Figure 8A:
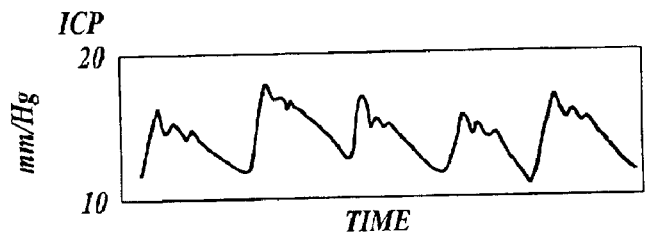
FIGS. 8A–8C show exemplary outputs from a system of the present invention providing clinically relevant information regarding ICP, ABP and autoregulation status.
Figure 8B:
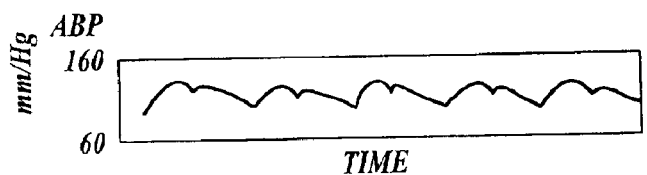
Figure 8C:
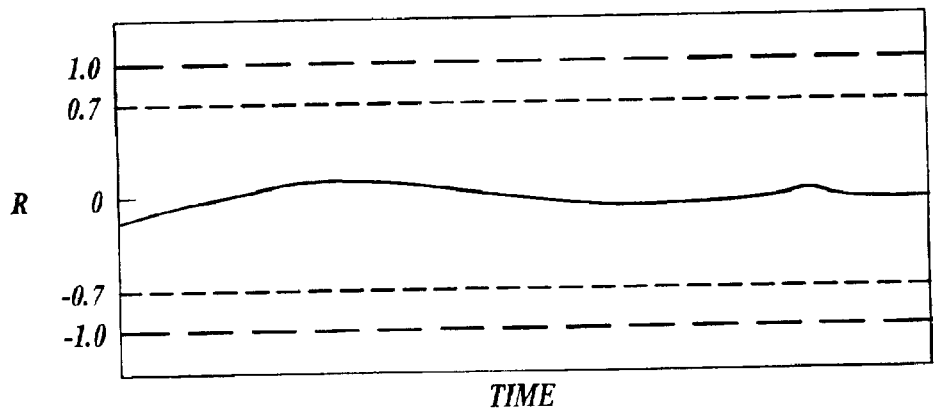

FIGS. 8A–8C show exemplary output displays for ICP (FIG. 8A), ABP (FIG. 8B) and autoregulation status (FIG. 8C). FIG. 8A shows a mean ICP of 15 mmHg, which is within the normal range. FIG. 8B shows a systolic pressure of 123 mmHg, a diastolic pressure of 75 mmHg, and a mean pressure of 91 mmHg, which is within the normal range. FIG. 8C shows an R correlation value of 0.3, which is within the normal range. The output display may show graphs of the collected data, as illustrated and may additionally or alternatively show normal or abnormal status, and be provided with a visual or audible alarm that is activated when ICP, ABP, autoregulation status values are outside predetermined thresholds.

Although the exemplary output displays illustrated in FIGS. 8A–8C include output data relating to ICP, ABP and autoregulation status, it will be understood that any one or combination of these outputs may be displayed in various devices, and that the displays may take other forms using alternative information. Methods and systems of the present invention may additionally be combined with other detection and monitoring systems to provide additional output data.

EXAMPLE 4

Methods for screening a patient population for anthrax infection and other infections associated with enlarged or painful tissue sites, such as lymphadenopathies, are provided. The high mortality rates associated with inhalational anthrax results, in part, from delays in diagnosis. Inhalational anthrax symptoms are similar to those associated other respiratory condition symptoms, such as the symptoms of various influenzas and pneumonia. Inhalational anthrax, however, unlike influenza and pneumonia, is characterized by enlarged mediastinal lymph nodes. The enlargement is generally severe and has a relatively early onset. Grinberg et al., *Quantitative pathology of inhalational anthrax I: quantitative microscopic findings*, Mod Pathol 14(5):482–95, May 2001. The lymphadenopathy associated with anthrax infection is believed to be painful. Hence, acoustic stimulation of pain may be used as an early indication of anthrax infection.

Using the acoustic palpation techniques described above, patients may be screened to determine whether they have lymphadenopathies that are painful. Various lymph nodes may be targeted and palpated to determine whether the lymph nodes are a source of pain. In particular, mediastinal lymph nodes may be targeted and palpated to determine whether they are painful. If so, additional diagnostic screening may be performed to confirm lymphadenopathies associated with anthrax infection or treatment may be initiated. This screening technique may be particularly useful for quickly screening patient populations to identify which patients should be subject to further diagnostic procedures or which should be treated first.

We claim:

1. A method for detecting a physiological property of a target tissue, comprising: noninvasively inducing a detectable tissue displacement at a central nervous system (CNS) target tissue site by applying an ultrasound pulse; noninvasively determining the induced tissue displacement at or in proximity to the CNS target tissue site; and relating the induced tissue displacement with a physiological property of the CNS target tissue.

2. A method of claim 1, wherein the induced tissue displacement is determined using an acoustic property of the target tissue.

3. A method of claim 2, wherein the induced tissue displacement is determined by administering a plurality of acoustic interrogation pulses to the target tissue site and collecting acoustic data from the target tissue site.

4. A method of claim 3, wherein the acoustic data relates to at least one of the amplitude, phase and frequency of acoustic scatter.

5. A method of claim 3, wherein the acoustic data relates to at least one parameter selected from the group consisting of: changes in the amplitude, phase or frequency of acoustic signals; changes in length of scattered acoustic signals relative to interrogation pulses; changes in primary and/or other maxima and/or minima amplitudes of an acoustic signal within a cardiac and/or respiratory cycle; ratios of the maximum and/or minimum amplitude to the mean or variance or distribution of acoustic signals within a cardiac cycle; and changes in temporal or spatial variance of scattered acoustic signals at different times in the same target tissue or at the same time in different target tissues.

6. A method of claim 3, wherein the induced tissue displacement is determined using at least one parameter selected from the group consisting of: a component of amplitude of the induced displacement; a rate of change of the displacement or subsequent relaxation of the target tissue; an amplitude or rate of change of a component of the shape of the induced displacement; a change in Fourier or wavelett representation of an acoustic scatter signal associated with the induced displacement; a property of induced second harmonic deformation; and time displacements of pulse echoes returning from the target tissue.

7. A method of claim 2, additionally comprising collecting acoustic data relating to the induced tissue displacement from the target tissue site using an ultrasound transducer operating in at least one of the following modes: transmission mode, reflection mode, scatter mode, backscatter mode, emission mode, echo mode, Doppler mode, color Doppler mode, harmonic or subharmonic imaging modes, a-mode, b-mode or m-mode; and correlating the acoustic data relating to the induced tissue displacement with a physiological property of the target tissue.

8. A method of claim 1, wherein the physiological property detected is intracranial pressure.

9. A method of claim 1, wherein the physiological property detected is cerebral perfusion pressure.

10. A method of claim 1, wherein the target tissue includes or is in proximity to a blood vessel and the physiological property detected is arterial blood pressure.

11. A method of claim 1, wherein the physiological property detected is selected from the group consisting of: vasospasm, stroke, local edema, infection, vasculitus, subdural or epidural hematomas, subarachnoid hemorrhages, ischemic conditions, multiple sclerosis, Alzheimers disease, hypoxic conditions, intracerebral hemorrhage, tumors and other intracranial masses, and acute, chronic and traumatic cranial conditions and injuries.

12. A method of claim 1, wherein the induced tissue displacement is determined using a detection technique selected from the group consisting of: near infrared spectroscopy (NIRS), optical coherence tomography (OCT), magnetic resonance techniques, and positron emission tomography (PET).

13. A method of claim 1, additionally comprising comparing the induced tissue displacement with an empirically determined standard.

14. A method of claim 1, additionally comprising determining the induced tissue displacement at different points in time relative to the inducement of a measurable tissue displacement.

15. A method of claim 1, additionally comprising inducing tissue displacement at a second target tissue site different from the first by applying a second ultrasound pulse, acquiring data relating to the induced tissue displacement at or in proximity to the second target tissue site, and comparing the acquired data relating to the tissue displaced at the target tissue site with the acquired data relating to the tissue displaced at the second target tissue site.

16. A method of claim 1, additionally comprising conducting an initial environmental assessment to evaluate the characteristics of the environment between an acoustic source and the target tissue site.

17. A method of claim 1, additionally comprising acquiring data relating to intrinsic tissue displacements at the target tissue site at multiple time points over the course of at least one cardiac cycle, and correlating the acquired data relating to the intrinsic tissue displacements and the induced tissue displacement at the target tissue site with a physiological property of the target tissue.

18. A method of claim 1, additionally comprising applying a plurality of different ultrasound pulses to the target tissue site and determining the tissue displacements induced by the different ultrasound pulses.

19. A method of claim 1, additionally comprising applying a plurality of ultrasound pulses to the target tissue site at a plurality of times and determining the induced tissue displacements.

20. A method of claim 1, additionally comprising applying a plurality of ultrasound pulses to a plurality of target tissue sites and measuring the induced tissue displacements at the plurality of target tissue sites.

21. A method for assessing intracranial pressure (ICP) in a subject, comprising: administering acoustic interrogation signals to a target CNS tissue site in the subject; detecting at least one of an acoustic emission, an induced and an intrinsic target tissue displacement based on acoustic data acquired from the target CNS tissue site; determining the arterial blood pressure (ABP) of the subject; and relating at least one of the acoustic emission, the induced and the intrinsic target tissue displacement and ABP with ICP.

22. A method of claim 21, additionally comprising processing the acoustic scatter data to assess the stiffness or elasticity of the target CNS tissue and relating the stiffness or elasticity of the target tissue with ICP.

23. A method of claim 21, additionally comprising comparing the ICP and ABP and determining the autoregulation status of the patient.

24. A method of claim 21, wherein the acoustic scatter data is acquired by administering a plurality of acoustic interrogation to the target tissue site and collecting acoustic data from the target CNS tissue site.

25. A method of claim 21, wherein the data relates to at least one of the magnitude, amplitude and phase of acoustic scatter.

26. A method of claim 21, wherein the acoustic scatter data is acquired using an ultrasound transducer operating in at least one of the following modes: transmission mode, reflection mode, scatter mode, backscatter mode, emission mode, echo mode, Doppler mode, color Doppler mode, harmonic or subharmonic imaging modes, a-mode, b-mode or m-mode.

27. A method of claim 21, additionally comprising acquiring multiple data sets, each data set relating to the acoustic scatter at different points in time.

28. A method of claim 21, additionally comprising conducting an initial environmental assessment to evaluate the characteristics of the environment between an acoustic source and the target tissue site.

29. A method of claim 21, additionally comprising acquiring data relating to tissue displacements at the target tissue site at multiple time points over the course of at least one cardiac cycle.

30. A method of claim 21, additionally comprising applying a plurality of ultrasound pulses to a plurality of CNS target tissue sites and acquiring data relating to the tissue displacements at the plurality of target tissue sites.

31. A method of claim 21, wherein the acoustic data relates to at least one parameter selected from the group consisting of: changes in the amplitude, phase or frequency of acoustic signals; changes in length of scattered acoustic signals relative to interrogation pulses; changes in primary and/or other maxima and/or minima amplitudes of an acoustic signal within a cardiac and/or respiratory cycle; ratios of the maximum and/or minimum amplitude to the mean or variance or distribution of acoustic signals within a cardiac cycle; and changes in temporal or spatial variance of scattered acoustic signals at different times in the same target tissue or at the same time in different target tissues.

32. A method of claim 21, wherein the induced tissue displacement is determined using at least one parameter selected from the group consisting of: a component of amplitude of the induced displacement; a rate of change of the displacement or subsequent relaxation of the target tissue; an amplitude or rate of change of a component of the shape of the induced displacement; a change in Fourier or wavelett representation of an acoustic scatter signal associated with the induced displacement; a property of induced second harmonic deformation; and time displacements of pulse echoes returning from the target tissue.

33. A system comprising an acoustic source and an acoustic detector, the acoustic source and detector being operably connected to a power source, the power source being operably connected to a function generator, and the function generator being operably connected to a controller having data acquisition, storage and analysis capability, the controller having the capability to process acquired acoustic data, make determinations of at least one of acoustic emission properties, induced and intrinsic tissue displacements and relate the determination of at least one of acoustic emission properties, induced and intrinsic tissue displacement(s) with at least one physiological tissue condition of a CNS target tissue, the controller being operably connected to a display device for displaying information relating to the at least one physiological tissue condition.

34. A system of claim 33, wherein an acoustic source and an acoustic detector are provided as an ultrasound transducer.

35. A system of claim 33, comprising multiple ultrasound transducers.

36. A system of claim 35, wherein the multiple ultrasound transducers are annular.

37. A system of claim 33, wherein an acoustic source and detector is provided as a transcranial Doppler device.

38. A system of claim 33, wherein the display device provides information relating to the ICP, ABP and autoregulation.

39. A system of claim 33, wherein the controller is capable of relating the tissue displacement(s) to at least one of ICP, arterial blood pressure (ABP) and cerebral perfusion pressure (CPP).

40. A system of claim 33, wherein the controller is capable of relating the tissue displacement(s) to intracranial pressure (ICP).

41. A system of claim 40, wherein the controller additionally acquires blood pressure data and relates the tissue displacement and blood pressure data to ICP.

42. A method for assessing a physiological property of a CNS target tissue, comprising the steps of:
(a) acquiring acoustic data relating to intrinsic tissue displacements at the CNS target tissue site at multiple time points over the course of at least one cardiac cycle; and
(b) relating the intrinsic tissue displacements with a physiological property of the CNS target tissue.
wherein said acoustic data is collected by using an ultrasound transducer.

43. The method of any of claims 42, wherein said ultrasound transducer operates in at least one of the following modes: transmission mode, reflection mode, scatter mode, backscatter mode, emission mode, echo mode, Doppler mode, color Doppler mode, harmonic or subharmonic imaging modes, a-mode, b-mode or m-mode.

44. The method of any of claims 42, further comprising the step of acquiring acoustic data at multiple target tissue sites at multiple time points over the course of at least one cardiac cycle.

45. The method of claim 42 wherein the acoustic data acquired relating to the intrinsic tissue displacement at the target tissue site relates to acoustic properties of the target tissue.

46. The method of any of claims 42, wherein said acoustic data is selected from the group consisting of changes in the amplitude of acoustic signals, changes in phase of acoustic signals, changes in frequency of acoustic signals, changes in acoustic emission signals, changes in length of scattered signals relative to an interrogation signal, changes in maximum and/or minimum amplitude of an acoustic signal within a cardiac cycle, the ratio of the maximum and/or minimum amplitude to that of the mean or variance of subsequent oscillations within a cardiac cycle, changes in temporal or spatial variance of scattered signals at different times in the same location and/or at the same time in different locations, and rates of change of tissue displacement or relaxation.

47. The method of any of claims 42, wherein said acoustic data is acquired by administering acoustic interrogation pulses to the target tissue site and collecting acoustic scatter data.

48. The method of claim 47 wherein said acoustic scatter data is acquired at a single acoustic frequency.

49. The method of claim 47 wherein said acoustic scatter data is acquired at multiple acoustic frequencies.

50. The method of any of claims 42, further comprising the step of relating the acoustic data and additional data relating to blood pressure, cardiac and/or respiratory cycles, to a physiological property of said target tissue.

51. The method of claim 42 wherein said target tissue includes or is in proximity to a blood vessel and wherein the physiological property detected is arterial blood pressure.

52. The method of any of claims 42 wherein said physiological property of said CNS tissue is selected from the group consisting of intracranial pressure, cerebral perfusion pressure, vasospasm, stroke, local edema, infection, vasculitus, subdural or epidural hematomas, subarachnoid hemorrhage, ischemic conditions, multiple sclerosis, Alzheimers disease, hypoxic conditions, intracerebral hemorrhage, tumors and other intracranial masses, and acute, chronic and traumatic conditions and injuries.

53. A method of claim 42, wherein the physiological property determined is ICP.

54. A method of claim 42, additionally comprising comparing the intrinsic tissue displacements with an empirically determined standard.

* * * * *

UNITED STATES PATENT AND TRADEMARK OFFICE
CERTIFICATE OF CORRECTION

PATENT NO. : 6,875,176 B2  Page 1 of 1
APPLICATION NO. : 09/995897
DATED : April 5, 2005
INVENTOR(S) : Pierre D. Mourad et al.

It is certified that error appears in the above-identified patent and that said Letters Patent is hereby corrected as shown below:

| Col. No. | Line(s) | Edits |
|---|---|---|
| 46 | 63 | Replace "interogation to the target" with --interogation pulses to the target-- |
| 48 | 23 | Replace "target tissue." with --target tissue,-- |
| 48 | 25 | Replace "any of claims 42" with --claim 42-- |
| 48 | 31 | Replace "any of claims 42" with --claim 42-- |
| 48 | 39 | Replace "any of claims 42" with --claim 42-- |
| 48 | 53 | Replace "any of claims 42" with --claim 42-- |
| 48 | 61 | Replace "any of claims 42" with --claim 42-- |
| 49 | 1 | Replace "any of claims 42" with --claim 42-- |

Signed and Sealed this

Twenty Second Day of April, 2008

JON W. DUDAS
*Director of the United States Patent and Trademark Office*